(12) United States Patent
Boraiah

(10) Patent No.: US 9,757,169 B2
(45) Date of Patent: *Sep. 12, 2017

(54) INTERLOCKING INTRAMEDULLARY ROD ASSEMBLY FOR PROXIMAL FEMORAL FRACTURES, INCLUDING UNSTABLE HIP FRACTURES

(71) Applicant: Sreevathsa Boraiah, Lake Grove, NY (US)

(72) Inventor: Sreevathsa Boraiah, Lake Grove, NY (US)

( * ) Notice: Subject to any disclaimer, the term of this patent is extended or adjusted under 35 U.S.C. 154(b) by 16 days.

This patent is subject to a terminal disclaimer.

(21) Appl. No.: 14/584,352

(22) Filed: Dec. 29, 2014

(65) Prior Publication Data

US 2015/0112345 A1    Apr. 23, 2015

Related U.S. Application Data

(63) Continuation-in-part of application No. 14/340,235, filed on Jul. 24, 2014.
(Continued)

(51) Int. Cl.
*A61B 17/74* (2006.01)
*A61B 17/72* (2006.01)

(52) U.S. Cl.
CPC .......... *A61B 17/748* (2013.01); *A61B 17/725* (2013.01); *A61B 17/744* (2013.01); *A61B 17/7225* (2013.01)

(58) Field of Classification Search
CPC . A61B 17/748; A61B 17/725; A61B 17/7241; A61B 17/7216; A61B 17/742;
(Continued)

(56) References Cited

U.S. PATENT DOCUMENTS 7,824,419 B2   11/2010   Boraiah
8,109,943 B2   2/2012   Boraiah et al.
(Continued)

OTHER PUBLICATIONS

Haidukewych et al., Reverse Obliquity Fractures of the Intertrochanteric Region of the Femur, The Journal of Bone and Joint Surgery, 2001, vol. 83-A, No. 5, pp. 643-650.
(Continued)

*Primary Examiner* — Julianna N Harvey
(74) *Attorney, Agent, or Firm* — Pandiscio & Pandiscio

(57) ABSTRACT

An interlocking intramedullary rod assembly for treating a fracture of a bone, the interlocking intramedullary rod assembly comprising: an intramedullary rod comprising a distal section and a proximal section; a distal interlocking screw comprising a distal end and a proximal end; and a proximal interlocking screw comprising a distal end and a proximal end; wherein the distal section of the intramedullary rod comprises a static distal seat for receiving the distal interlocking screw, and the proximal section of the intramedullary rod comprises a dynamic proximal seat for receiving the proximal interlocking screw; and further wherein the static distal seat is configured to secure the distal interlocking screw to the intramedullary rod such that the distal interlocking screw cannot move relative to the intramedullary rod, and the dynamic proximal seat is configured to secure the proximal interlocking screw to the intramedullary rod such that the angle between the distal end of the proximal interlocking screw and the proximal section of the intramedullary rod can be reduced but not increased. The proximal interlocking screw can provide dual plane compression at the fracture site, which includes linear compression at the fracture site and angular compression at the fracture site. The angular compression can be effected either during the surgery or after the surgery when the patient weightbears.

25 Claims, 14 Drawing Sheets

Related U.S. Application Data

(60) Provisional application No. 61/958,281, filed on Jul. 24, 2013.

(58) Field of Classification Search
CPC ............ A61B 17/7225; A61B 17/7233; A61B 17/744
See application file for complete search history.

(56) References Cited

U.S. PATENT DOCUMENTS

| | | |
|---|---|---|
| 2002/0107578 A1 | 8/2002 | Speitling et al. |
| 2007/0049940 A1 | 3/2007 | Wallace et al. |
| 2007/0213757 A1 | 9/2007 | Boraiah |
| 2009/0048600 A1* | 2/2009 | Matityahu .......... A61B 17/7241 606/62 |
| 2010/0262166 A1 | 10/2010 | Boraiah et al. |
| 2011/0196370 A1 | 8/2011 | Mikhail |
| 2012/0265202 A1* | 10/2012 | Schwammberger . A61B 17/744 606/64 |
| 2014/0330274 A1 | 11/2014 | Matityahu et al. |

OTHER PUBLICATIONS

Kregor et al., Unstable Pertrochanteric Femoral Fractures, Journal of Orthopaedic Trauma, 2005, vol. 19, No. 1, pp. 63-66.

\* cited by examiner

INTERLOCKING INTRAMEDULLARY ROD ASSEMBLY FOR PROXIMAL FEMORAL FRACTURES, INCLUDING UNSTABLE HIP FRACTURES

REFERENCE TO PENDING PRIOR PATENT APPLICATIONS

This patent application is a continuation-in-part of pending prior U.S. patent application Ser. No. 14/340,235, filed Jul. 24, 2014 by Sreevathsa Boraiah for INTERLOCKING INTRAMEDULLARY ROD ASSEMBLY FOR PROXIMAL FEMORAL FRACTURES, INCLUDING UNSTABLE HIP FRACTURES, which patent application claims benefit of prior U.S. Provisional Patent Application Ser. No. 61/958,281, filed Jul. 24, 2013 by Sreevathsa Boraiah for TENSION BAND NAIL: FOR PROXIMAL FRACTURES INCLUDING UNSTABLE HIP FRACTURES.

The two (2) above-identified patent applications are hereby incorporated herein by reference.

FIELD OF THE INVENTION

The present invention relates generally to an interlocking intramedullary rod assembly for treatment of fractures of a long bone, and more particularly to an interlocking intramedullary rod assembly for treating proximal femoral fractures including unstable hip fractures. The interlocking intramedullary rod assembly can also be utilized in other applications in the body where the biomechanical principals of tension banding apply. The interlocking intramedullary rod assembly can also be used in situations where a fracture is to be at least partially reduced after introduction of the intramedullary rod, with fracture reduction being effected either by the surgeon or as a result of weight bearing. Even more particularly, the present invention relates to a load-bearing interlocking intramedullary rod assembly which comprises an intramedullary rod which is inserted into the intramedullary canal of a fractured proximal femur for treatment of a proximal femur fracture.

BACKGROUND OF THE INVENTION

Hip fractures present significant healthcare issues. These healthcare issues includes mortality, morbidity and increased healthcare costs. Improvements to the rate of reliable healing would significantly benefit patient health and reduce healthcare costs.

Proximal fractures of the femur are traditionally treated with either (i) an intramedullary rod (sometimes referred to as an intramedullary nail) which is positioned in the intramedullary canal of the femur, or (ii) a plate applied to the side of the femur and fixed in place with one or more screws set into the femur. The choice of using an intramedullary rod or a plate and screw is generally based on the location and complexity of the fracture.

As noted above, the intramedullary rod is placed in the intramedullary canal of the femur and typically provides excellent mechanical stability for the bone. Among other things, the intramedullary rod exhibits good weight-sharing properties. However, the use of an intramedullary rod also involves a more complex surgical procedure and higher cost.

Plates such as the Dynamic Hip Screw (DHS) plate are generally simpler to deploy and less expensive than intramedullary rods. Plates generally work well for stable intertrochanteric fractures. However, in subtrochanteric fractures and unstable intertrochanteric fractures, it is difficult to achieve proper compression of the fracture site with plates upon the application of weight. Therefore, most subtrochanteric fractures and unstable intertrochanteric fractures are treated with intramedullary rods.

When the treatment of subtrochanteric fractures and unstable intertrochanteric fractures by intramedullary rods is unsuccessful, the fractures are typically treated with tension band plates (such as a tension band blade plate) which utilize the geometry of the femoral subtrochanteric region and the compressive forces imposed by the surrounding musculature. A tension band construct, by definition, utilizes tensile forces and converts them into compressive forces. At an advanced level, when a tension band blade plate is applied to the tension side of the femur and pressure is thereafter applied, the tension band blade plate converts the tension forces into compressive forces which can be used to stabilize the fracture. Tension band blade plates are known to be effective in treating proximal femoral fractures. However, installation of these tension band blade plates requires substantial technical skill and involves a more complex operation. Therefore, the use of tension band blade plates is generally not suited for index surgery (i.e., the first surgery performed after the occurrence of a fracture), and is best suited for revising failed fracture repairs.

It is believed that a device that can combine the mechanical advantages of intramedullary rods with the mechanical advantages of tension band blade plates would be extremely useful for treating all kinds of proximal femoral fractures, including not only the aforementioned subtrochanteric fractures and unstable intertrochanteric fractures, but also including stable intertrochanteric fractures and other types of proximal femoral fractures. Such a device would also be extremely useful for treating fractures of other bones in the body. For the sake of clarity, even though the present invention may be used for all hip fractures (including stable and unstable intertrochanteric fractures, subtrochanteric fractures, and other types of proximal femoral fractures), and even though the present invention may be used for fractures of other bones in the body, the following discussion of the present invention will focus on subtrochanteric fractures and unstable intertrochanteric fractures.

Intramedullary rods have evolved over time. The first generation of intramedullary rods essentially involved inserting a solid rod down the intramedullary canal of the femur. This type of intramedullary rod is relatively primitive and only grossly aligns the bone. The first generation of intramedullary rods does not control motion at the fracture line in any specific plane.

The second generation of intramedullary rods was the dynamic interlocking intramedullary rod. The dynamic interlocking intramedullary rod allows for compression of the bone at the fracture site by allowing axial compression of the fracture. This axial compression of the fracture is achieved through the use of lag screws which pass through the bone, across the intramedullary rod and back into the bone. However, existing lag screw constructs do not control the coronal plane motion of the unstable and subtrochanteric fractures. Studies have shown that the dynamic interlocking intramedullary rod has not been as effective as desired. More particularly, for the repair of subtrochanteric fractures and fractures of the femoral neck or femoral head using a dynamic interlocking intramedullary rod, the intramedullary rod is driven into the femur from the proximal end and a femoral neck pin is introduced into the femoral head via the femoral neck of the femur, with the femoral neck pin passing through a bore formed in the intramedullary rod at an oblique angle to the axis of the intramedullary rod. The dynamic interlocking intramedullary rod, when placed under a load, is subjected to a combined stress which is composed of compressive and tensile stresses and shear loads. In the case of delayed healing and overload, a crack or fissure may develop in the bone, namely at the site at which the highest shear stress occurs. Current dynamic interlocking intramedullary rods do not provide any kind of unique biomechanical advantage for fracture healing in unstable intertrochanteric and subtrochanteric fractures except acting as an intramedullary buttress. The dynamic interlocking intramedullary rod does not offer any anatomic site-specific advantage for healing of the fracture.

The present invention addresses this biomechanical problem by reducing the shear loads on the intramedullary rod and provides a more stable biomechanical environment for a more accelerated and reliable healing of the fracture.

SUMMARY OF THE INVENTION

It is an object of the present invention to provide a novel interlocking intramedullary rod assembly for the treatment of a proximal femur fracture whereby the interlocking intramedullary rod assembly exhibits load bearing properties and creates a biomechanically-conducive environment for reliable fracture healing.

In one form of the present invention, the new interlocking intramedullary rod assembly comprises an intramedullary rod that is positioned in the intramedullary canal of the femur, a distal interlocking screw that locks the distal part of the intramedullary rod to the distal femur, and a proximal interlocking screw which secures the intramedullary rod to the proximal femur in a new and unique manner. More particularly, the intramedullary rod is placed in the intramedullary canal of the femur antegrade (i.e., distally from the proximal trochanter). The intramedullary rod has an approximately 12 degree bend at its proximal end to accommodate the natural geometry of the proximal femur. After the intramedullary rod has been placed in the intramedullary canal of the femur, the proximal interlocking screw is deployed. The proximal interlocking screw is a lag screw and is advanced from the lateral aspect of the femur through a dynamic proximal seat formed in the intramedullary rod and then into the femoral head. This dynamic proximal seat extends lateral-to-medial, and has a circular configuration on its medial end and a slot configuration on its lateral end. The dynamic proximal seat is referred to as a "dynamic" seat inasmuch as this seat allows for selected motion of the proximal interlocking screw relative to the intramedullary rod. The proximal interlocking screw is placed at an angle of approximately 124-127 degrees to the longitudinal axis of the intramedullary rod, based on the patient's anatomy. The angle between the intramedullary rod and the proximal interlocking screw is pre-selected by the surgeon after templating pre-operative radiographs. Note that this is a fixed angle for any given intramedullary rod and proximal interlocking screw combination. Therefore, the surgeon will select the appropriate intramedullary rod and proximal interlocking screw combination from inventory. After the proximal interlocking screw is deployed in the dynamic proximal seat, the distal interlocking screw is deployed in the distal part of the intramedullary rod. The distal interlocking screw is placed from the lateral side of the femur through a static distal seat in the intramedullary rod and into the medial side of the femur. The static distal seat in the distal part of the intramedullary rod extends lateral-to-distal and comprises a circular opening on its medial end and a circular opening on its lateral end. The static distal seat is referred to as a "static" seat inasmuch as this seat does not allow for motion of the distal interlocking screw relative to the intramedullary rod.

In accordance with the present invention, after the proximal interlocking screw is inserted into the dynamic proximal seat at an angle of between approximately 124-127 degrees to the longitudinal axis of the intramedullary rod, the surgeon may choose to further change the angle at which the proximal interlocking screw extends through the dynamic proximal seat (e.g., up to approximately 138 degrees) depending on the patient's anatomy, fracture configuration and the opposition of fracture fragments. Also, upon the application of weight (i.e., when the patient stands), the proximal interlocking screw shifts position within the dynamic proximal seat in order to allow a partial reduction of the fracture, e.g., within the given range of approximately 124-138 degrees. Angular locking means are provided for locking the proximal interlocking screw relative to the intramedullary rod. The proximal interlocking screw can be locked to the intramedullary rod at various stages of the procedure, e.g., (i) when the surgeon deems that the angle subtended at the insertion is good, or (ii) after the surgeon increases the valgus angle (if the surgeon deems that the option needs to exist to further increase the valgus angle after weight bearing, then the angular locking means are left open), or (iii) upon weight bearing, the fracture settles into its desired valgus, whereupon the proximal interlocking screw can be locked to the intramedullary rod.

In one preferred form of the invention, there is provided an interlocking intramedullary rod assembly for treating a fracture of a bone, said interlocking intramedullary rod assembly comprising:

an intramedullary rod comprising a distal section and a proximal section;

a distal interlocking screw; and a proximal interlocking screw;

wherein said distal section of said intramedullary rod comprises a static distal seat for receiving said distal interlocking screw, and said proximal section of said intramedullary rod comprises a dynamic proximal seat for receiving said proximal interlocking screw;

and further wherein said static distal seat is configured to secure said distal interlocking screw to said intramedullary rod such that said distal interlocking screw cannot move relative to said intramedullary rod, and said dynamic proximal seat is configured to secure said proximal interlocking screw to said intramedullary rod such that a first end of said proximal interlocking screw cannot move relative to said intramedullary rod and the second end of said proximal interlocking screw can move relative to said intramedullary rod.

In another preferred form of the invention, there is provided a method for treating a fracture in the proximal femur, said method comprising:

providing an interlocking intramedullary rod assembly comprising:

an intramedullary rod comprising a distal section and a proximal section;

a distal interlocking screw; and a proximal interlocking screw;

wherein said distal section of said intramedullary rod comprises a static distal seat for receiving said distal interlocking screw, and said proximal section of said intramedullary rod comprises a dynamic proximal seat for receiving said proximal interlocking screw;

and further wherein said static distal seat is configured to secure said distal interlocking screw to said intramedullary rod such that said distal interlocking screw cannot move relative to said intramedullary rod, and said dynamic proximal seat is configured to secure said proximal interlocking screw to said intramedullary rod such that a first end of said proximal interlocking screw cannot move relative to said intramedullary rod and the second end of said proximal interlocking screw can move relative to said intramedullary rod;

positioning said intramedullary rod in the intramedullary canal of the femur so that said distal section of said intramedullary rod resides within the shaft of the femur and said proximal section of said intramedullary rod resides within a proximal portion of the femur;

inserting said proximal interlocking screw through the proximal portion of the femur, through said dynamic proximal seat and into the proximal portion of the femur, and inserting said distal interlocking screw through the shaft of the femur, through said static distal seat and into the shaft of the femur; and adjusting the disposition of said proximal interlocking screw within said dynamic proximal seat so as to at least partially reduce the fracture.

In another preferred form of the invention, there is provided an interlocking intramedullary rod assembly for treating a fracture of a bone, said interlocking intramedullary rod assembly comprising:

an intramedullary rod comprising a distal section and a proximal section;

a distal interlocking screw comprising a distal end and a proximal end; and a proximal interlocking screw comprising a distal end and a proximal end;

wherein said distal section of said intramedullary rod comprises a static distal seat for receiving said distal interlocking screw, and said proximal section of said intramedullary rod comprises a dynamic proximal seat for receiving said proximal interlocking screw;

and further wherein said static distal seat is configured to secure said distal interlocking screw to said intramedullary rod such that said distal interlocking screw cannot move relative to said intramedullary rod, and said dynamic proximal seat is configured to secure said proximal interlocking screw to said intramedullary rod such that the angle between said distal end of said proximal interlocking screw and said proximal section of said intramedullary rod can be reduced but not increased.

In another preferred form of the invention, there is provided a method for treating a fracture in the proximal femur, said method comprising:

providing an interlocking intramedullary rod assembly comprising:

an intramedullary rod comprising a distal section and a proximal section;

a distal interlocking screw comprising a distal end and a proximal end; and a proximal interlocking screw comprising a distal end and a proximal end;

wherein said distal section of said intramedullary rod comprises a static distal seat for receiving said distal interlocking screw, and said proximal section of said intramedullary rod comprises a dynamic proximal seat for receiving said proximal interlocking screw;

and further wherein said static distal seat is configured to secure said distal interlocking screw to said intramedullary rod such that said distal interlocking screw cannot move relative to said intramedullary rod, and said dynamic proximal seat is configured to secure said proximal interlocking screw to said intramedullary rod such that the angle between said distal end of said proximal interlocking screw and said proximal section of said intramedullary rod can be reduced but not increased;

positioning said intramedullary rod in the intramedullary canal of the femur so that said distal section of said intramedullary rod resides within the shaft of the femur and said proximal section of said intramedullary rod resides within a proximal portion of the femur;

inserting said proximal interlocking screw through the proximal portion of the femur, through said dynamic proximal seat and into the proximal portion of the femur, and inserting said distal interlocking screw through the shaft of the femur, through said static distal seat and into the shaft of the femur; and adjusting the disposition of said proximal interlocking screw within said dynamic proximal seat so as to at least partially reduce the fracture.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention comprises the provision and use of a novel interlocking intramedullary rod assembly for treating proximal femoral fractures and other fractures in the body, wherein the fracture is treated with the use of an intramedullary rod and interlocking screws of the novel interlocking intramedullary rod assembly.

Interlocking Intramedullary Rod Assembly 5

Figure 1:
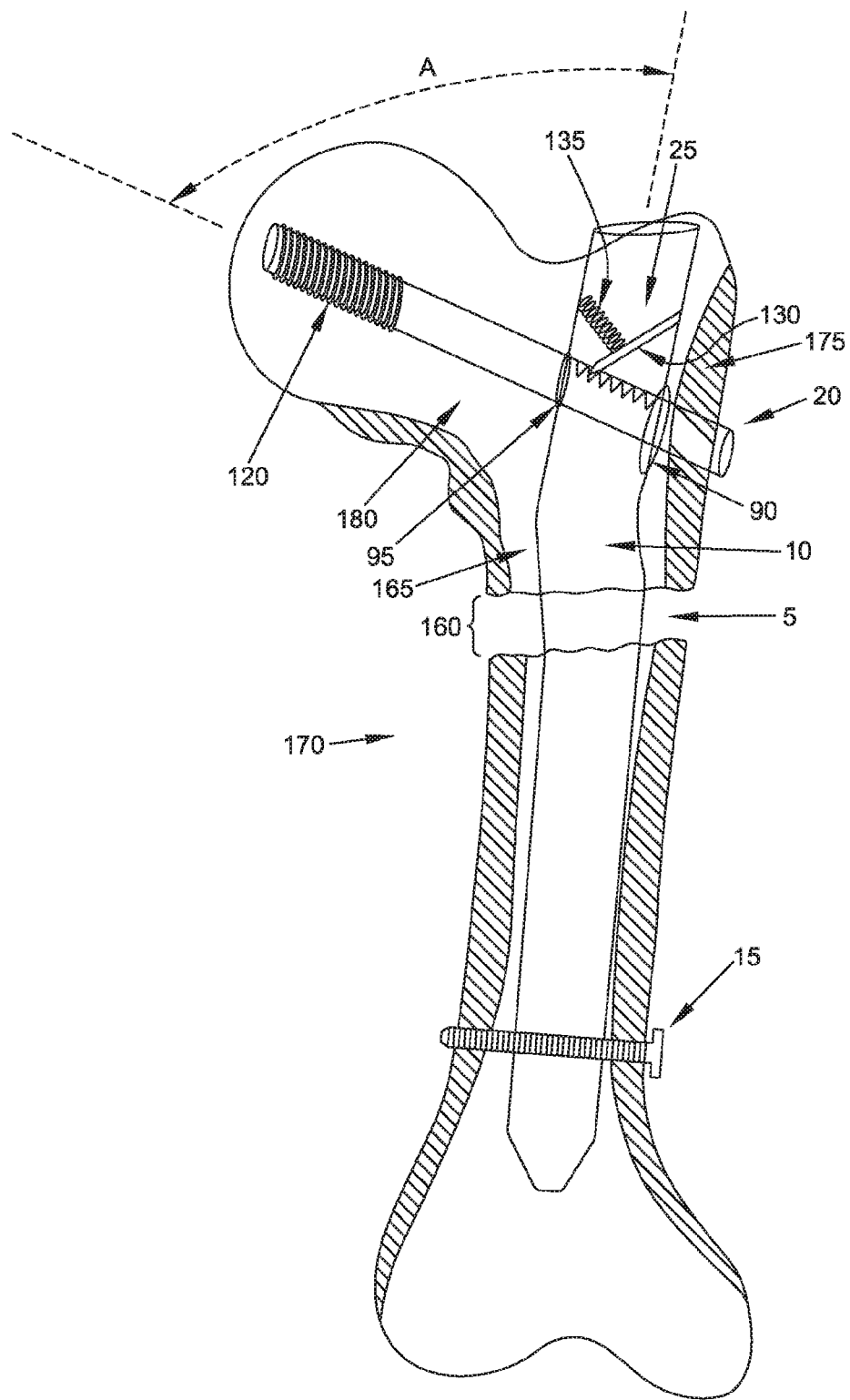
FIG. 1 is a schematic view showing a novel interlocking intramedullary rod assembly formed in accordance with the present invention, with the novel interlocking intramedullary rod assembly being disposed in a fractured femur, and with the interlocking intramedullary rod assembly and the fractured femur being shown prior to partial reduction of the fracture.

Looking first at FIG. 1, there is shown a novel interlocking intramedullary rod assembly 5 formed in accordance with the present invention. Novel interlocking intramedullary rod assembly 5 generally comprises an intramedullary rod 10, a distal interlocking screw 15, a proximal interlocking screw 20 and a locking finger 25 mounted to intramedullary rod 10 for selectively engaging proximal interlocking screw 20 as will hereinafter be discussed.

1. The Intramedullary Rod

Figure 2:
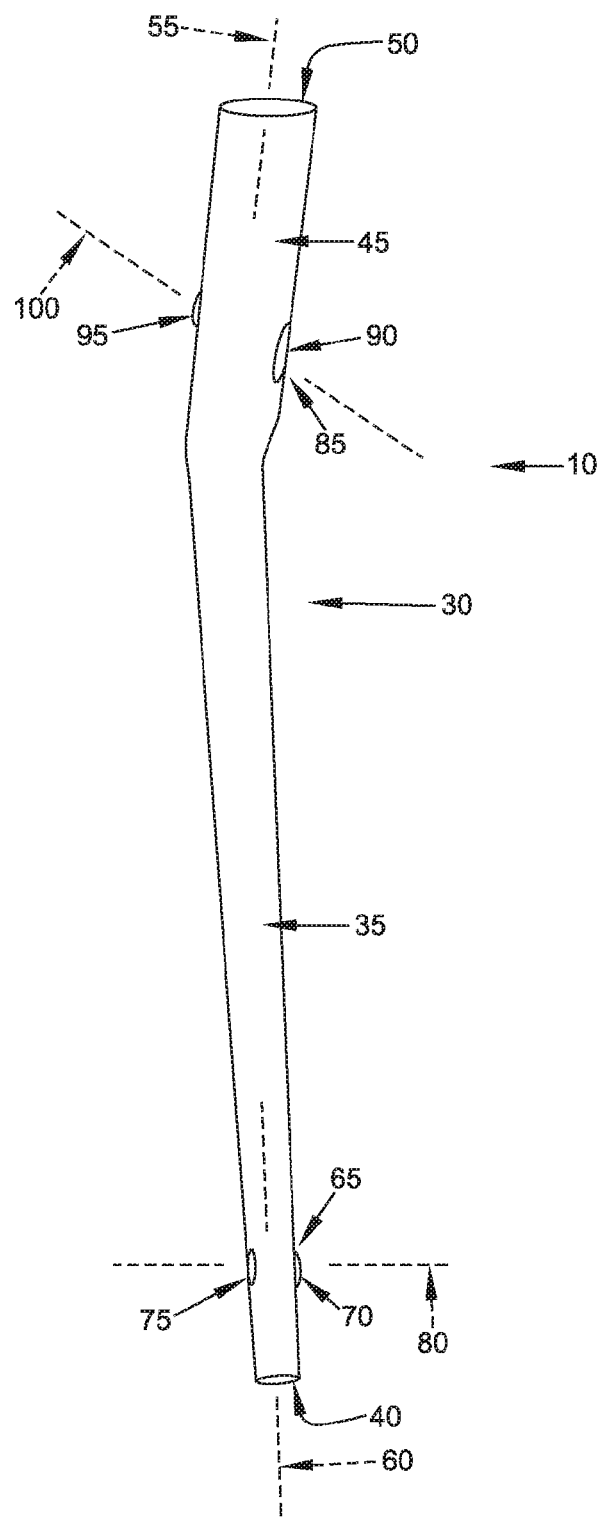
FIG. 2 is a schematic view showing the intramedullary rod of the novel interlocking intramedullary rod assembly of FIG. 1.

Looking now at FIGS. 1 and 2, intramedullary rod 10 generally comprises a shaft 30 having a distal section 35 terminating in a distal end 40 and a proximal section 45 terminating in a proximal end 50. Distal section 35 and proximal section 45 are formed integral with one another. The longitudinal axis 55 of proximal section 45 is offset from the longitudinal axis 60 of distal section 35 (e.g., at an approximately 12 degree angle). The length and diameters of distal section 35 and proximal section 45, and the degree of offset of the longitudinal axis 55 of proximal section 45 from the longitudinal axis 60 of distal section 35, are dependent on the size of the bone receiving intramedullary rod 10, such that intramedullary rod 10 may be deployed in an antegrade fashion down the intramedullary canal of the femur of a patient, with distal section 35 being disposed in the shaft of the femur and proximal section 45 being disposed in the proximal femur (e.g., in the trochanteric area). In one preferred form of the invention, proximal section 45 has a larger diameter than distal section 35. And in one preferred form of the invention, distal section 35 and proximal section 45 are both tapered, and their respective tapers are coordinated so as to form a substantially smooth taper across the length of intramedullary rod 10.

Preferably intramedullary rod 10 is hollow along its length, from distal end 40 to proximal end 50.

Distal section 35 comprises a static distal seat 65 for receiving distal interlocking screw 15 as distal interlocking screw 15 passes through a lateral portion of the femur, across distal section 35 of intramedullary rod 10 and into a medial portion of the femur (FIG. 1). To this end, static distal seat 65 comprises a round opening 70 on the lateral side of distal section 35 and a round opening 75 on the medial side of distal section 35. Round openings 70 and 75 are disposed on an axis 80 which preferably extends substantially perpendicular to the longitudinal axis 60 of distal section 35. In one preferred form of the invention, round openings 70 and 75 are of the same size, such that static distal seat 65 essentially comprises a cylindrical seat. Furthermore, round openings 70 and 75 are sized relative to distal interlocking screw 15 such that distal interlocking screw 15 will be unable to move relative to intramedullary rod 10 when distal interlocking screw 15 is disposed in static distal seat 65.

Proximal section 45 comprises a dynamic proximal seat 85 for receiving proximal interlocking screw 20 as proximal interlocking screw 20 passes through a lateral portion of the femur, across proximal section 45 of intramedullary rod 10 and into a medial portion of the femur (FIG. 1). To this end, dynamic proximal seat 85 comprises a slot opening 90 on the lateral side of proximal section 45 and a round opening 95 on the medial side of proximal section 45. Slot opening 90 is larger than round opening 95 in the proximal-to-distal direction, such that dynamic proximal seat 85 essentially comprises an offset frustorectangular seat. Furthermore, round opening 95 is sized relative to proximal interlocking screw 20, and slot opening 90 is sized relative to proximal interlocking screw 20, such that when proximal interlocking screw 20 is disposed in dynamic proximal seat 85, proximal interlocking screw 20 will be substantially unable to move relative to round opening 95 but will be able to move relative to slot opening 90. The center of slot opening 90 and the center of round opening 95 are disposed on an axis 100 which is set at an angle of approximately 124-137 degrees to the longitudinal axis 55 of proximal section 45. The locus of fixation of proximal interlocking screw 20 with intramedullary rod 10 is via the medial round opening 95 in intramedullary rod 10. As will hereinafter be discussed, when proximal interlocking screw 20 is disposed in dynamic proximal seat 85, proximal interlocking screw 20 will initially reside in the proximal portion of slot opening 90 on the lateral side of intramedullary rod 10, and in round opening 95 on the medial side of the intramedullary rod. After load is applied (either by the surgeon to change the angle of proximal interlocking screw 20 with intramedullary rod 10 or when the patient weightbears), the bone will shift so that proximal interlocking screw 20 will thereafter reside in the distal portion of slot opening 90 on the lateral side of the intramedullary rod and in round opening 95 on the medial side of the intramedullary rod.

2. The Distal Interlocking Screw

Figure 3:
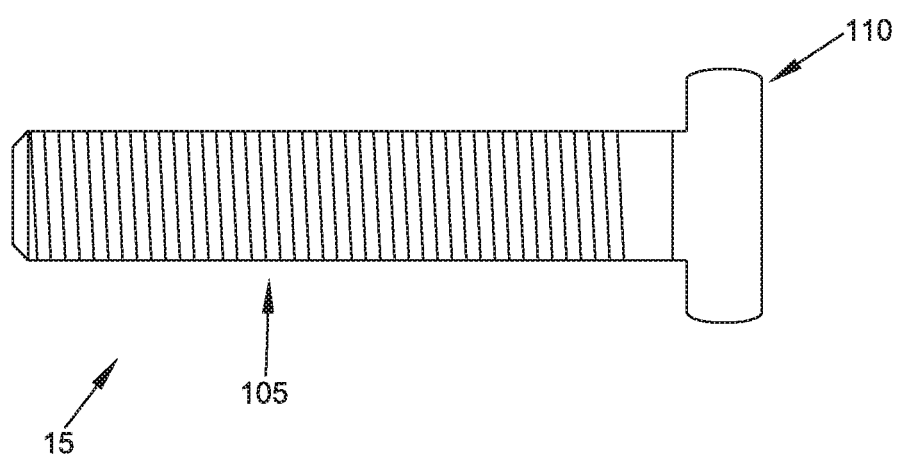
FIG. 3 is a schematic view showing the distal interlocking screw of the novel interlocking intramedullary rod assembly of FIG. 1.

Looking next at FIGS. 1 and 3, distal interlocking screw 15 is designed to be deployed in static distal seat 65 of distal section 35 of intramedullary rod 10. To this end, distal interlocking screw 15 comprises a threaded shaft 105 terminating in a head 110.

3. The Proximal Interlocking Screw

Figure 4:
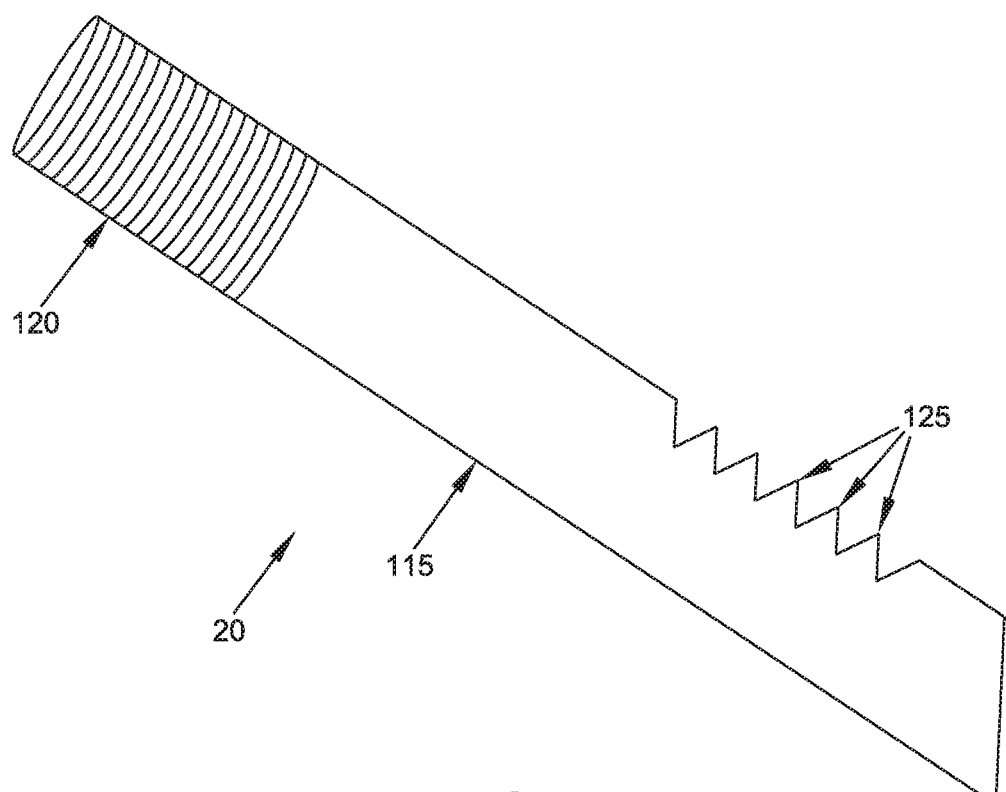
FIG. 4 is a schematic view showing the proximal interlocking screw of the novel interlocking intramedullary rod assembly of FIG. 1.

Looking next at FIGS. 1 and 4, proximal interlocking screw 20 is designed to be deployed in dynamic proximal seat 85 of proximal section 45 of intramedullary rod 10. To this end, proximal interlocking screw 20 comprises a shaft 115 having threads 120 on its distal end and ratchet teeth 125 on its proximal end.

If desired, proximal interlocking screw 20 may be hollow.

4. The Locking Finger

As noted above, angular locking means are provided for locking proximal interlocking screw 20 relative to intramedullary rod 10, i.e., within dynamic proximal seat 85.

Figure 5:
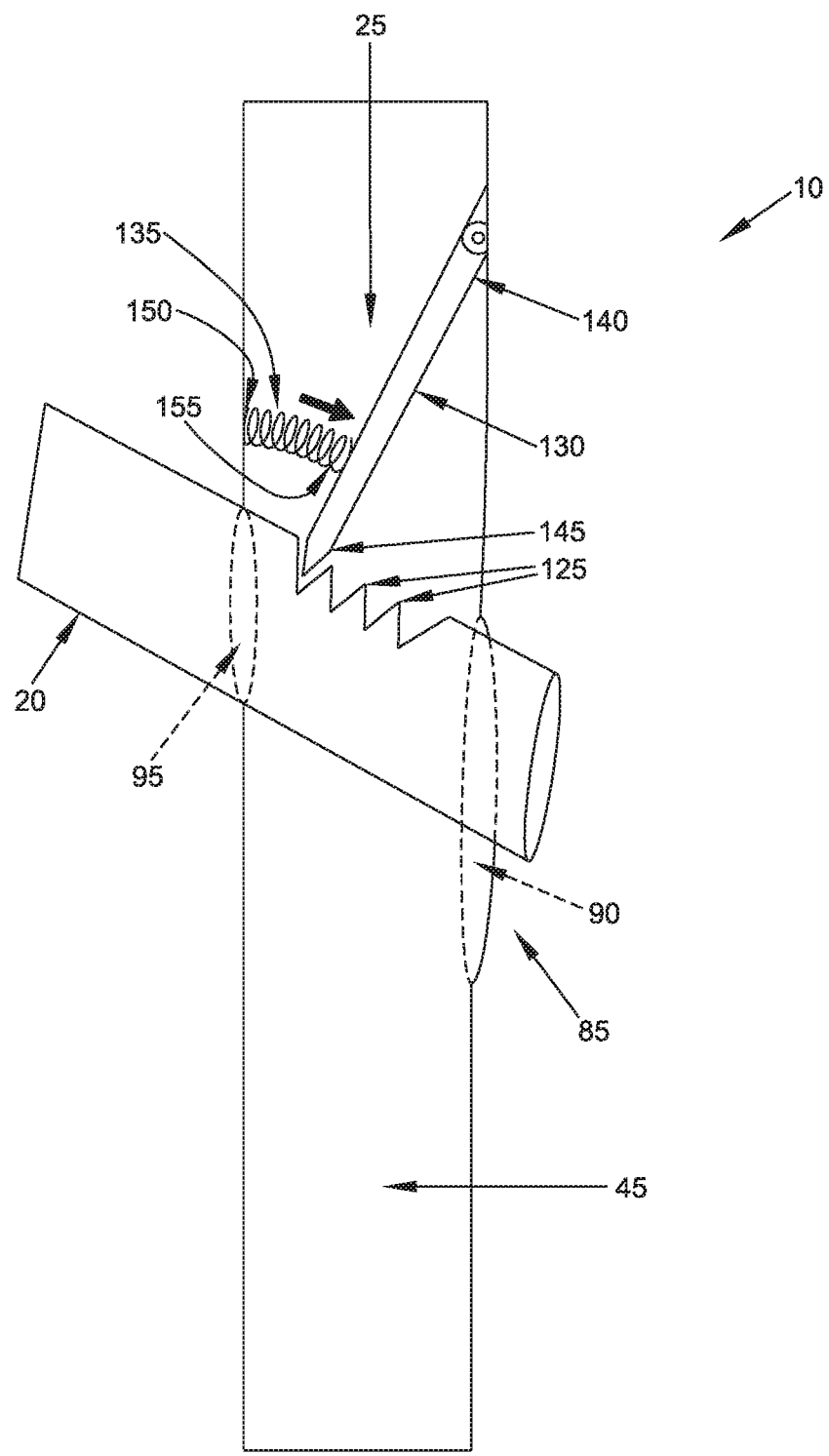
FIG. 5 is a schematic view showing the locking finger which comprises an exemplary embodiment of the angular locking means of the novel interlocking intramedullary rod assembly of FIG. 1.

To this end, and looking next at FIGS. 1 and 5, in one preferred form of the invention, a locking finger 25 is provided for engaging proximal interlocking screw 20 when proximal interlocking screw 20 is disposed in dynamic proximal seat 85. Locking finger 25 is mounted within proximal section 45 of intramedullary rod 10 and serves to engage proximal interlocking screw 20 as will hereinafter be discussed. Locking finger 25 allows for a specific kind of motion between proximal interlocking screw 20 and intramedullary rod 10 (and hence a specific kind of motion between the proximal end of the femur and the distal end of the femur).

More particularly, locking finger 25 generally comprises a lever 130 and a spring 135. One end 140 of lever 130 is pivotally mounted to the lateral side of intramedullary rod 10 (e.g., to the lateral side wall of proximal section 45) so as to allow for angular movement of lever 130 relative to intramedullary rod 10. The free end 145 of lever 130 engages the teeth 125 on proximal interlocking screw 20 with a one-way action as will hereinafter be discussed. This one-way action is the result of lever 130 being under constant lateral pressure from spring 135, as will also hereinafter be discussed.

Spring 135 is also mounted within proximal section 45 of intramedullary rod 10. One end 150 of spring 135 is mounted to the medial side of intramedullary rod 10 (e.g., to the medial side wall of proximal section 45), and the other end 155 of spring 135 is mounted to lever 135 so as to bias lever 135 laterally (i.e., counterclockwise from the angle of view of FIG. 5).

5. The Mechanism of Tension Banding Using Interlocking Intramedullary Rod Assembly The mechanism of tension banding using interlocking intramedullary rod assembly 5 will now be discussed. For the purposes of example but not limitation, the mechanism of tension banding using interlocking intramedullary rod assembly 5 will be discussed in the context of a subtrochanteric fracture gap model, i.e., a 1 cm fracture gap 160 (FIG. 1) in the subtrochanteric area 165 of a femur 170.

First, intramedullary rod 10 is inserted into the fractured femur as shown in FIG. 1.

Second, proximal interlocking screw 20 is inserted, lateral-to-medial, through a lateral portion 175 of the femur, across dynamic proximal seat 85 in proximal section 45 of intramedullary rod 10 and then into the medial portion 180 of femur 170. Note that proximal interlocking screw 20 is inserted adjacent the proximal end of lateral slot opening 90 (FIGS. 1 and 5) and through medial round opening 95 until the threaded distal end 120 of proximal interlocking screw 20 is secured in the femoral head. As this occurs, the advancing proximal interlocking screw 20 engages lever 130 and forces the free end 145 of lever 130 medially, against the power of spring 135, with the free end 145 of lever 130 engaging teeth 125 formed in proximal interlocking screw 20. Note that teeth 125 prevent lever 130 from returning laterally under the power of spring 135.

Third, distal interlocking screw 15 is inserted, lateral-to-medial, through a lateral portion of the femur, across distal seat 65 (FIG. 2) in distal section 35 and into a medial portion of the femur. Note that distal interlocking screw 15 is securely mounted to distal section 35 of intramedullary rod 10 (by virtue of the disposition of distal interlocking screw 15 in circular openings 70 and 75 of intramedullary rod 10) as well as to the lateral and medial portions of the femur.

At this point, interlocking intramedullary rod assembly 5 and femur 170 are in the positions shown in FIGS. 1 and 5.

Figure 6:
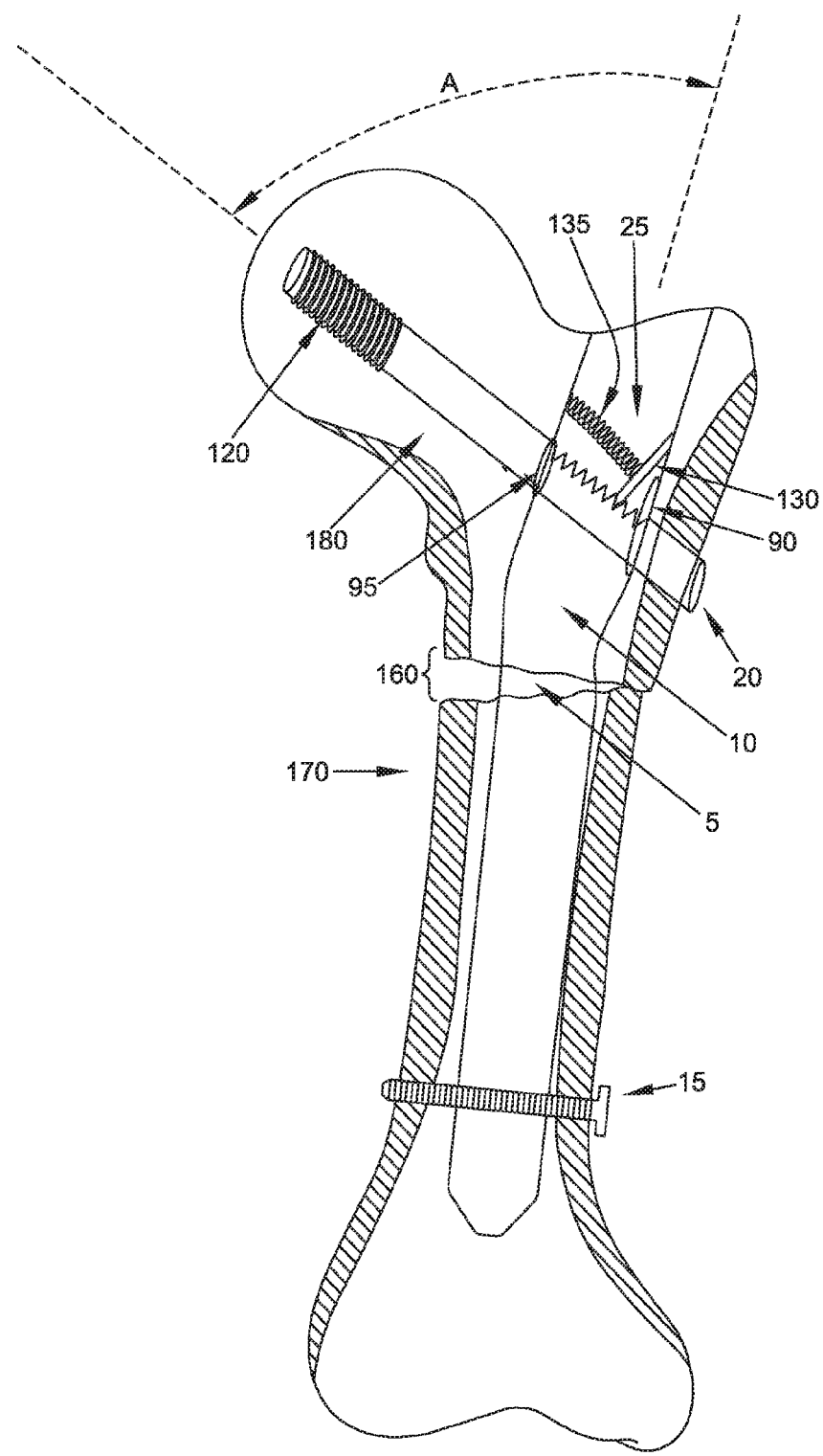
FIG. 6 is a schematic view like that of FIG. 1, except showing the interlocking intramedullary rod assembly and the fractured femur after partial reduction of the fracture.

Upon the application of force to the proximal end of the femur (e.g., by the surgeon during the procedure or upon the application of weight to the proximal end of the femur), the stress at the fracture site increases. Since the medial portion of dynamic proximal seat 85 is circular (i.e., round hole 95), the medial portion of dynamic proximal seat 85 acts as a static hole, preventing any kind of angular motion between proximal interlocking screw 20 and the medial wall of the femur. However, since the lateral portion of dynamic proximal seat 85 is a slot (i.e., slot opening 90), proximal interlocking screw 20 will slide inferiorly in lateral slot opening 90. This will create an angular collapse of the fracture site (FIG. 6). Significantly, as this angular collapse of the fracture site occurs, the free end 145 of lever 130 is moved counterclockwise (from the angle of view of FIG. 6) by spring 135. The free end 145 of lever 130 slides along the distally-moving teeth 125 of proximal interlocking screw 20 until, at the limit of the angular collapse, the free end of lever 130 lodges in teeth 125. Thereafter, when surgeon-applied force or weight-applied force is no longer applied to the proximal end of the femur, lever 130 and spring 135 prevent the bone from returning to its original fracture disposition, i.e., lever 130 and spring 135 cooperate with teeth 125 on proximal interlocking screw 20 to prevent any upward movement of proximal interlocking screw 20 within slot opening 90 on the lateral side of the femur.

Thus it will be seen that interlocking intramedullary rod assembly 5 creates a one-way angular collapse of the proximal fracture fragment into valgus, i.e., into an outward angulation of the distal portion of the femur. The center of rotation of the proximal fracture fragment is through of the point where proximal interlocking screw 20 engages the medial round opening 95 of intramedullary rod 10. The valgus collapse of the fracture is accompanied by the following dynamic processes:

(i) valgus collapse—the medial fracture gap is maintained, the lateral fracture gap is decreased;

(ii) proximal interlocking screw 20 moves distally in slot opening 90 on the lateral side of intramedullary rod 10;

(iii) the position of lever 130 changes with respect to teeth 125, i.e., the disposition of lever 130 changes and engages different teeth as the result of the distal movement of the lateral end of proximal interlocking screw 20; and (iv) intramedullary rod 10 is medialized in the intramedullary canal of the femur.

Thus it will be seen that novel interlocking intramedullary rod assembly 5 combines the mechanical advantages of intramedullary rods with the mechanical advantages of tension banding, whereby to provide a device which is capable of treating all kinds of proximal femoral fractures (including not only subtrochanteric fractures and unstable intertrochanteric fractures, but also stable intertrochanteric fractures and other types of proximal femoral fractures), as well as treating fractures of other bones in the body.

Interlocking Intramedullary Rod Assembly 205

In the construction shown in FIGS. 1-6, the angle A (FIGS. 1 and 6) between proximal interlocking screw 20 and proximal section 45 of intramedullary rod 10 can be reduced (e.g., by the application of weight to the joint), but the provision of locking finger 25 (comprising lever 130 and spring 135) prevents the angle A from re-opening (e.g., when weight is removed). Thus, interlocking intramedullary rod assembly 5 effectively provides a dynamic, one-way mechanism for continuously capturing fracture-closing forces (e.g., such as those generated by the application of weight) until healing occurs.

Figure 7:
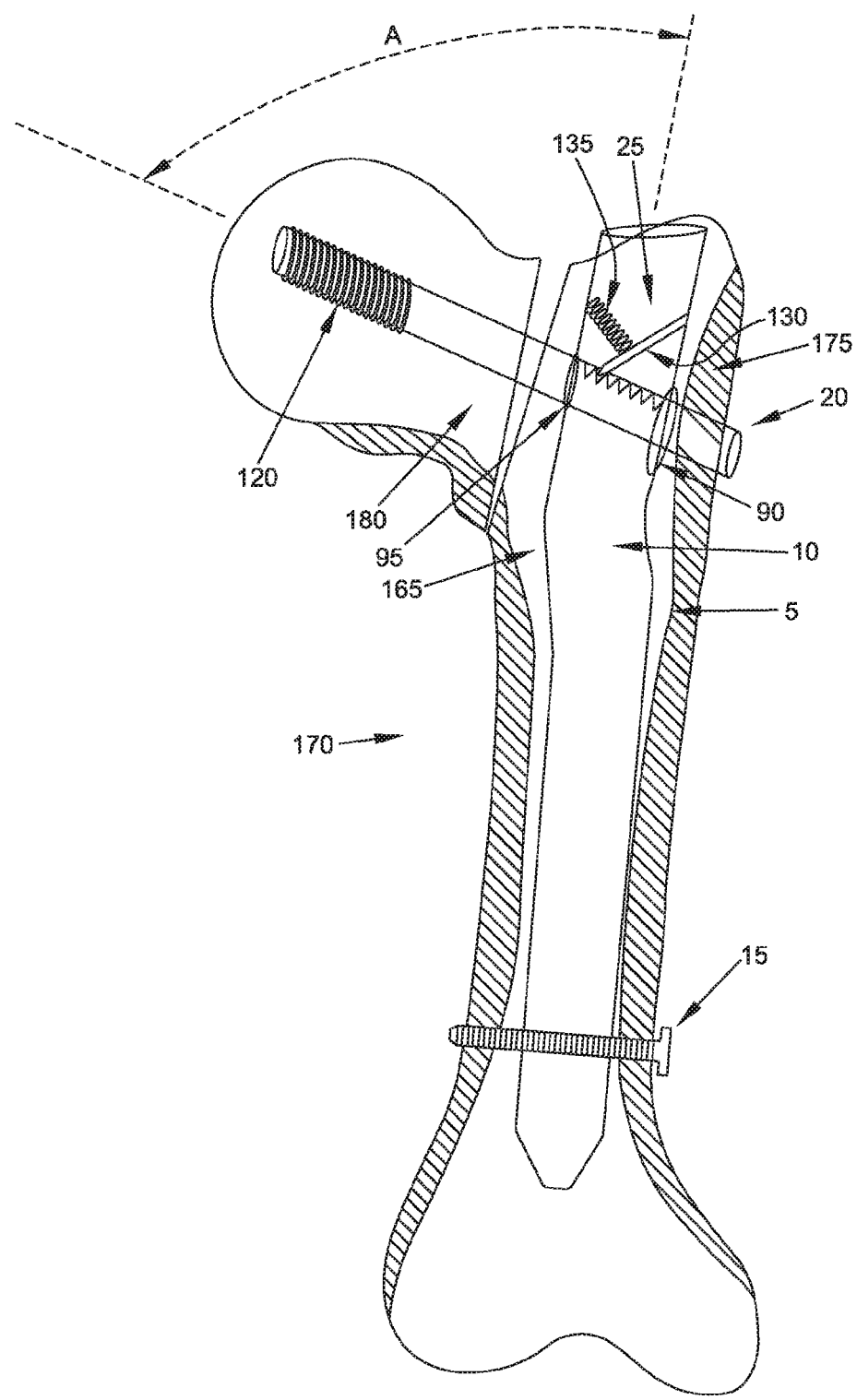
FIG. 7 is a schematic view showing the novel interlocking intramedullary rod assembly of FIGS. 1-6 disposed in a fractured femur, wherein the femur is fractured across the femoral neck.
Figure 8:
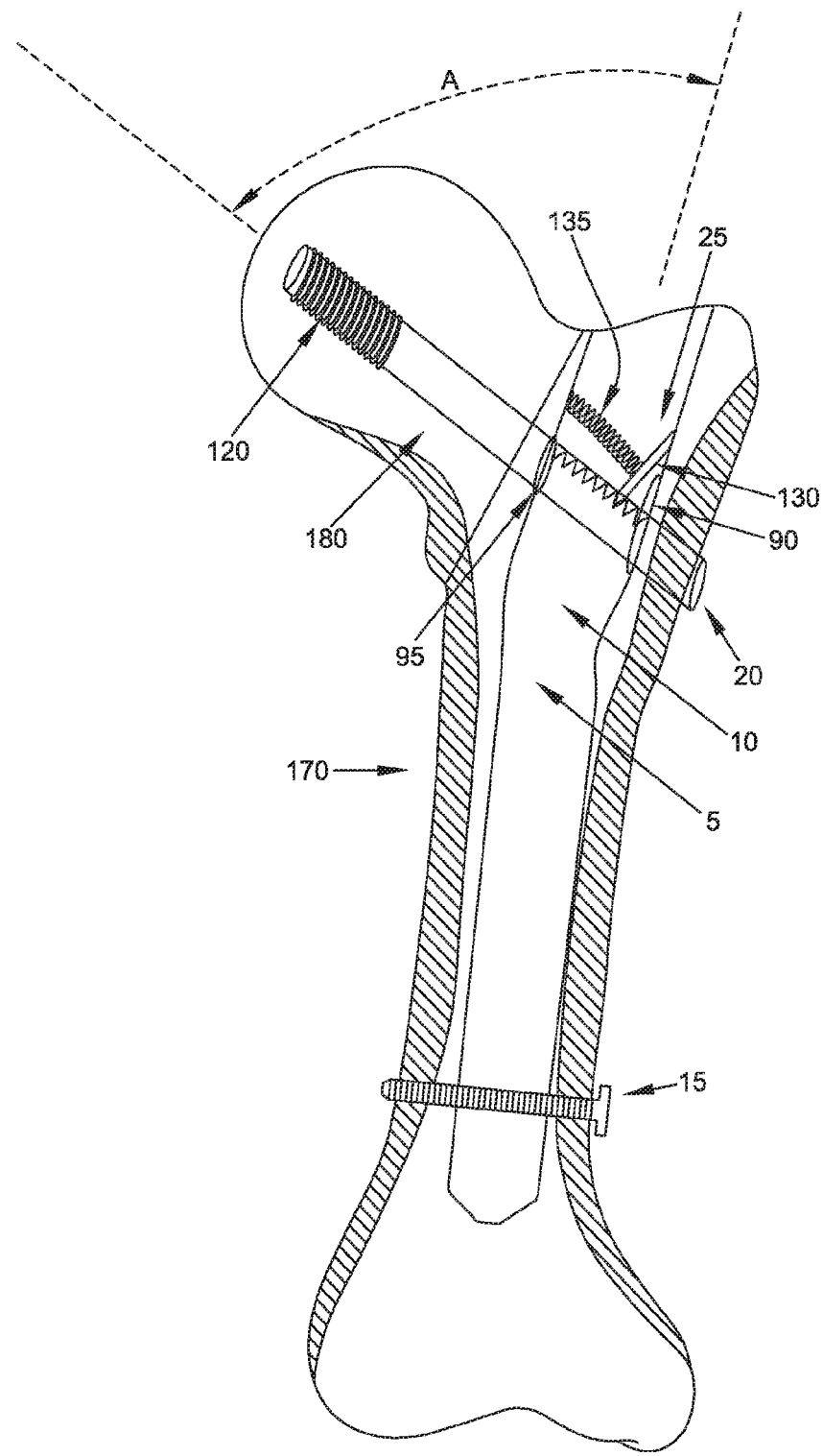
FIG. 8 is a schematic view like that of FIG. 7, except showing the novel interlocking intramedullary rod assembly and the fractured femur after reduction of the fracture.

In addition to the foregoing, the interlocking intramedullary rod assembly 5 discussed above is shown in FIGS. 1-6 in the context of reducing a fracture extending across the width of the femoral shaft. However, the interlocking intramedullary rod assembly 5 can also be used to reduce a fracture extending across the femoral neck. See, for example, FIGS. 7 and 8. In this situation, the application of weight causes the angle A between proximal interlocking screw 20 and proximal section 45 of intramedullary rod 10 to be reduced, but locking finger 25 prevents the angle A from re-opening when weight is removed. Thus, interlocking intramedullary rod assembly 5 again provides a dynamic, one-way mechanism for continuously capturing fracture-closing forces (e.g., such as those generated by the application of weight) until healing occurs.

In some situations, it may be desirable for the surgeon to reduce the fracture during the procedure in which interlocking intramedullary rod assembly 5 is deployed in the patient. In theory, the surgeon could manipulate the patient's leg so as to force the angle of the fracture closed (i.e., so as to reduce the angle A). However, in practice, it can be difficult for the surgeon to manipulate the patient's leg sufficiently to reduce the fracture in this manner.

To this end, and looking now at FIGS. 9-14, there is provided an interlocking intramedullary rod assembly 205 which provides the surgeon with a convenient way in which to reduce the fracture during the surgical procedure in which the interlocking intramedullary rod assembly 205 is deployed in the patient, while also retaining the ability to capture the fracture-closing forces generated by the application of weight.

Figure 9:
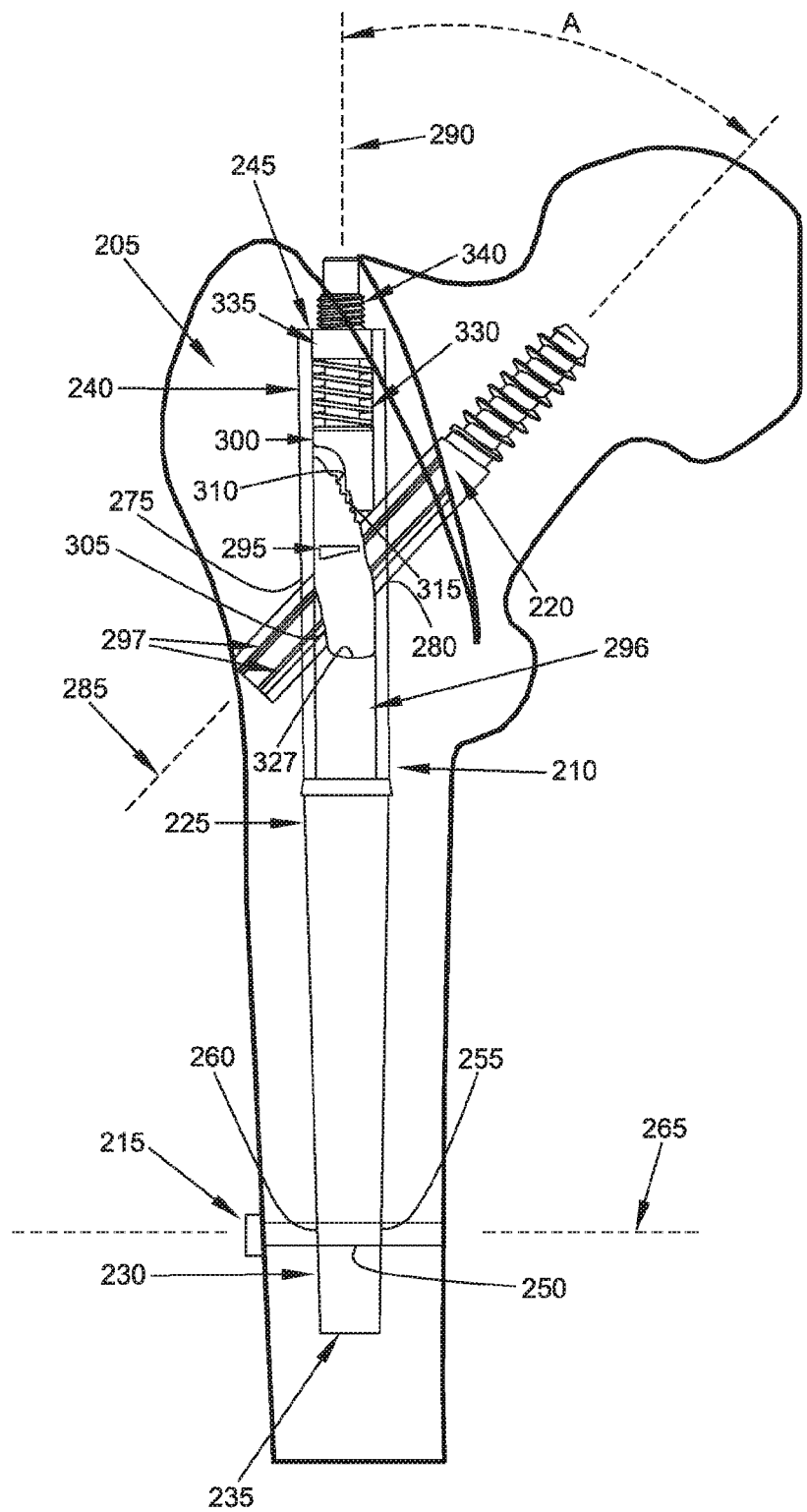
FIGS. 9 and 10 are schematic views showing another novel interlocking intramedullary rod assembly formed in accordance with the present invention, with the novel interlocking intramedullary rod assembly being disposed in a fractured femur, wherein the femur is fractured across the femoral neck, and further wherein the interlocking intramedullary rod assembly and the fractured femur are shown prior to reduction of the fracture.
Figure 10:
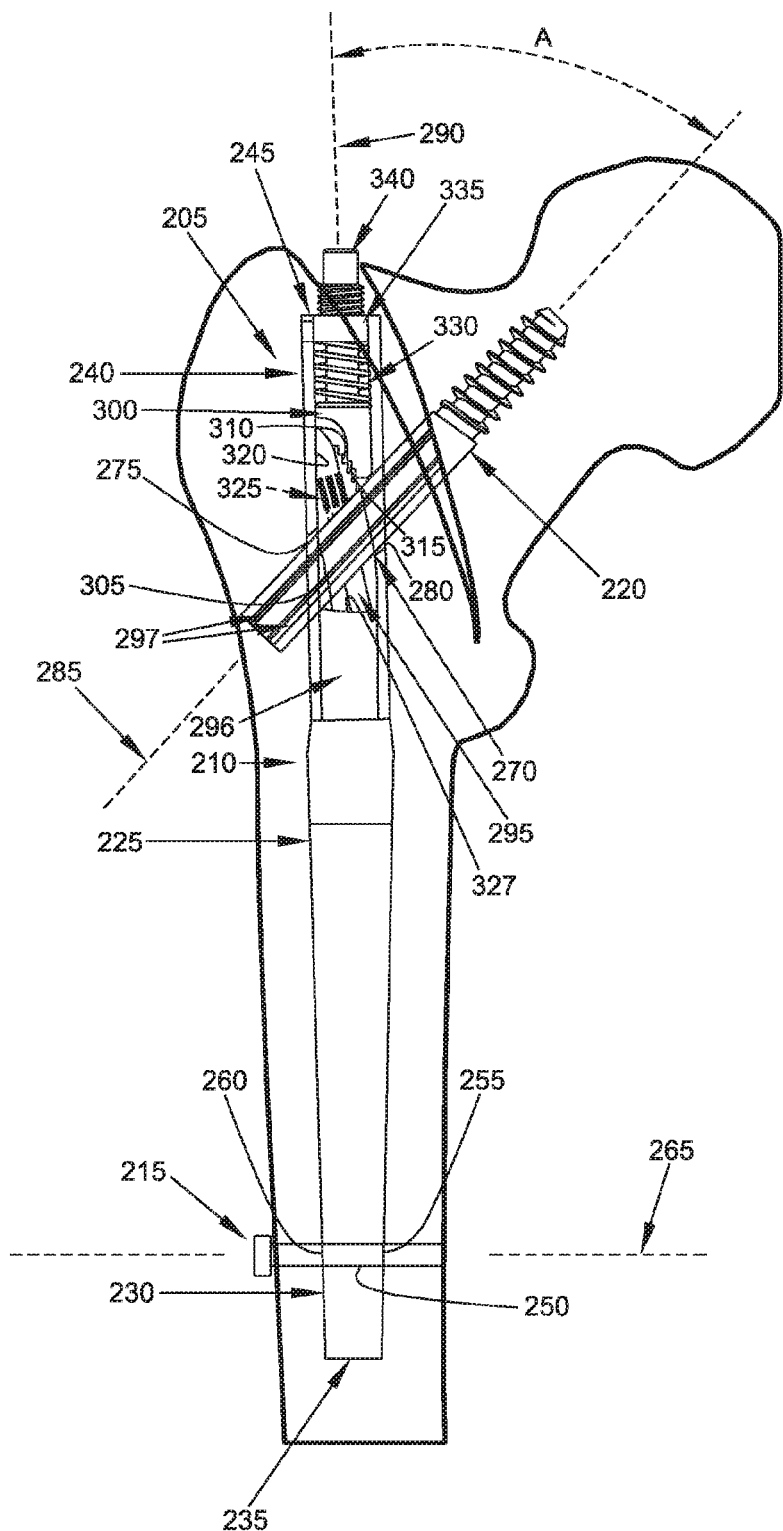

More particularly, in this form of the invention, and looking now at FIGS. 9 and 10, interlocking intramedullary rod assembly 205 generally comprises an intramedullary rod 210, a distal interlocking screw 215 and a proximal interlocking screw 220.

Intramedullary rod 210 generally comprises a shaft 225 having a distal section 230 terminating in a distal end 235, and a proximal section 240 terminating in a proximal end 245. Distal section 230 and proximal section 240 are preferably formed integral with one another. The length and diameters of distal section 230 and proximal section 240 are dependent upon the size of the bone receiving intramedullary rod 210, such that intramedullary rod 210 may be deployed in an antegrade fashion down the intramedullary canal of the femur of the patient, with distal section 230 being disposed in the shaft of the femur and proximal section 240 being disposed in the proximal femur (e.g., in the trochanteric area).

Preferably intramedullary rod 210 is hollow along its length from distal end 235 to proximal end 245.

Distal section 230 of intramedullary rod 210 comprises a static distal seat 250 for receiving distal interlocking screw 215 as distal interlocking screw 215 passes through a lateral portion of the femur, across distal section 230 of intramedullary rod 210 and into a medial portion of the femur. To this end, static distal seat 250 comprises a round opening 255 on the lateral side of distal section 230 and a round opening 260 on the medial side of distal section 230. Round openings 255, 260 are disposed on an axis 265 which preferably extends substantially perpendicular to the longitudinal axis of distal section 230 of intramedullary rod 210. In one preferred form of the invention, round openings 255, 260 are the same size, such that static distal seat 250 essentially comprises a cylindrical seat. Furthermore, round openings 255, 260 are sized relative to distal interlocking screw 215 such that distal interlocking screw 215 will be unable to move relative to intramedullary rod 210 when distal interlocking screw 215 is disposed in static distal seat 250.

Proximal section 240 of intramedullary rod 210 comprises a dynamic proximal seat 270 for receiving proximal interlocking screw 220 as proximal interlocking screw 220 passes through a lateral portion of the femur, across proximal section 240 of intramedullary rod 210 and into a medial portion of the femur. To this end, dynamic proximal seat 270 comprises a slot opening 275 on the lateral side of proximal section 240 and a round opening 280 on the medial side of proximal section 240. Slot opening 275 is larger than round opening 280 in the proximal-to-distal direction, such that dynamic proximal seat 270 essentially comprises an angled, tapering seat narrowing from a larger slot opening 275 on the lateral side of the bone to a smaller round opening 280 on the medial side of the bone. Furthermore, round opening 280 is sized relative to proximal interlocking screw 220, and slot opening 275 is sized relative to proximal interlocking screw 220, such that when proximal interlocking screw 220 is disposed in dynamic proximal seat 270, proximal interlocking screw 220 will be substantially unable to move relative to round opening 280 but will be able to move relative to slot opening 275. The center of slot opening 275 and the center of round opening 280 are disposed on an axis 285 which is set at an angle of approximately 124-137 degrees to the longitudinal axis 290 of proximal section 240 of intramedullary rod 210. The locus of fixation of proximal interlocking screw 220 with intramedullary rod 210 is via the medial round opening 280 in intramedullary rod 210 as well as via a carrier 295 (see below) in the proximal section 240 of intramedullary rod 210. As will hereinafter be discussed, when proximal interlocking screw 220 is disposed in dynamic proximal seat 270, proximal interlocking screw 220 will initially reside in the proximal portion of slot opening 275 on the lateral side of intramedullary rod 210 and round opening 280 on the medial side of intramedullary rod 210. After load is applied (either by the surgeon to change the angle A between proximal interlocking screw 220 and intramedullary rod 210, or when the patient weight-bears), the bone will shift so that proximal interlocking screw 220 will thereafter reside in the distal portion of slot opening 275 on the lateral side of intramedullary rod 210 and in round opening 280 on the medial side of intramedullary rod 210.

In order to provide the desired dynamic, one-way motion between proximal interlocking screw 220 and intramedullary rod 210 (i.e., in order to ensure that the angle A between proximal interlocking screw 220 and intramedullary rod 210 can be reduced but not re-opened), intramedullary rod 210 comprises (i) a carrier 295 for receiving proximal interlocking screw 220, the carrier being selectively pivotable within intramedullary rod 210, (ii) a saddle 296 for supporting carrier 295 within intramedullary rod 210 so that carrier 295 is pivotable within intramedullary rod 210, and (iii) a stepper 300 for allowing carrier 295 to pivot in one direction within intramedullary rod 210 but preventing carrier 295 from pivoting in an opposite direction within intramedullary rod 210.

More particularly, carrier 295 is rotatably disposed within the interior of intramedullary rod 210 and comprises a cylindrical opening 305 extending therethrough for receiving proximal interlocking screw 220. Cylindrical opening 305 of carrier 295 is generally aligned with dynamic proximal seat 270 in intramedullary rod 210. Carrier 295 also comprises a ridged, angled proximal surface 310 for engaging a ridged, angled distal surface 315 of stepper 300. In addition, carrier 295 comprises a groove 320 and a set screw 325. Set screw 325, accessible through groove 320, is located in the central hollow portion of carrier 295 and, when advanced into contact with proximal interlocking screw 220, engages one of a plurality of slots 297 formed in proximal interlocking screw 220, whereby to allow proximal interlocking screw 220 to move longitudinally within intramedullary rod 210, but prevents proximal interlocking screw 220 from rotation along the longitudinal axis of the screw once set screw 325 engages one of the slots 297 formed in the proximal interlocking screw 220.

Saddle 296 is disposed within intramedullary rod 210 and comprises a curved proximal surface 327 which supports carrier 295 within intramedullary rod 210 so that carrier 295 is pivotable within intramedullary rod 210.

Stepper 300 is movably disposed within intramedullary rod 210 on the proximal side of carrier 290. A spring 330 is disposed between stepper 300 and a cap 335 which is mounted to the distal end of intramedullary rod 210. Spring 330 forces stepper 300 distally, so that ridged distal surface 315 of stepper 300 engages the ridged proximal surface 310 of carrier 295. As a result, when load is applied (either by the surgeon manipulating the leg to change the angle A between proximal interlocking screw 220 and intramedullary rod 210, or when the patient weightbears), carrier 295 will pivot clockwise (from the angle of view of FIGS. 9, 10, 13 and 14) within intramedullary rod 210 due to the movement of proximal interlocking screw 220 relative to intermedullary rod 210, and stepper 300 will be moved distally by spring 330, whereby to prevent carrier 295 from pivoting counterclockwise (from the angle of view of FIGS. 9, 10, 13 and 14), and hence prevent proximal interlocking screw 220 from pivoting so as to re-open the angle A.

In addition to the foregoing, a push rod 340 is also provided so as to permit the surgeon to manually push (either directly or indirectly) on proximal interlocking screw 220, whereby to cause proximal interlocking screw 220 to pivot clockwise (from the angle of view of FIGS. 9, 10, 13 and 14) and thereby change the aforementioned angle A. More particularly, in one preferred form of the invention, push rod 340 extends through an opening (not shown) in stepper 300 and another opening (not shown) in carrier 295 so as to be able to engage proximal interlocking screw 220 directly. Advancing push rod 340 against proximal interlocking screw 220 causes proximal interlocking screw 220 to pivot clockwise (from the angle of view of FIGS. 9, 10, 13 and 14) and thereby change the aforementioned angle A. As this occurs, carrier 295 pivots within intramedullary rod 210 to accommodate for the change in angle A. When this happens, stepper 300 (which is under the tension of spring 330) will move downward within intramedullary rod 210, constantly engaging stepper 300 and preventing carrier 295 from pivoting back (i.e., from pivoting counterclockwise from the angle of view of FIGS. 9, 10, 13 and 14).

Alternatively, if desired, push rod 340 can extend through an opening (not shown) in stepper 300 so as to be able to engage angled proximal surface 310 of carrier 295—in this form of the invention, moving push rod 340 distally against angled proximal surface 310 of carrier 295 cams carrier 295 so that carrier 295 pivots within intramedullary rod 210, whereby to cause proximal interlocking screw 220 to pivot and thereby change the aforementioned angle A. Thus, in this form of the invention, push rod 340 "indirectly" pushes on proximal interlocking screw 220, whereby to change the aforementioned angle A.

Thus, in this form of the invention, the provision of carrier 295 and stepper 300 permits the angle A between proximal interlocking screw 220 and intramedullary rod 210 to be reduced, but prevents the angle A from re-opening. Furthermore, in this form of the invention, this dynamic, one-way action can be achieved by changing the disposition of proximal interlocking screw 220 (e.g., by weightbearing, by the surgeon manipulating the patient's limb, etc.) or by using push rod 340 to (either directly or indirectly) pivot proximal interlocking screw 220 clockwise (from the angle of view of FIGS. 9, 10, 13 and 14) relative to intramedullary rod 210 so as to close the angle A. It will be appreciated that when push rod 340 pivots proximal interlocking screw 220 clockwise (from the angle of view of FIGS. 9, 10, 13 and 14) relative to intramedullary rod 210, carrier 295 also pivots clockwise (from the angle of view of FIGS. 9, 10, 13 and 14), and stepper 300 moves distally (under the power of spring 330) within intramedullary rod 210 to prevent carrier 295 from pivoting back (i.e., counterclockwise, from the angle of view of FIGS. 9, 10, 13 and 14), and hence preventing angle A from reopening.

Figure 11:
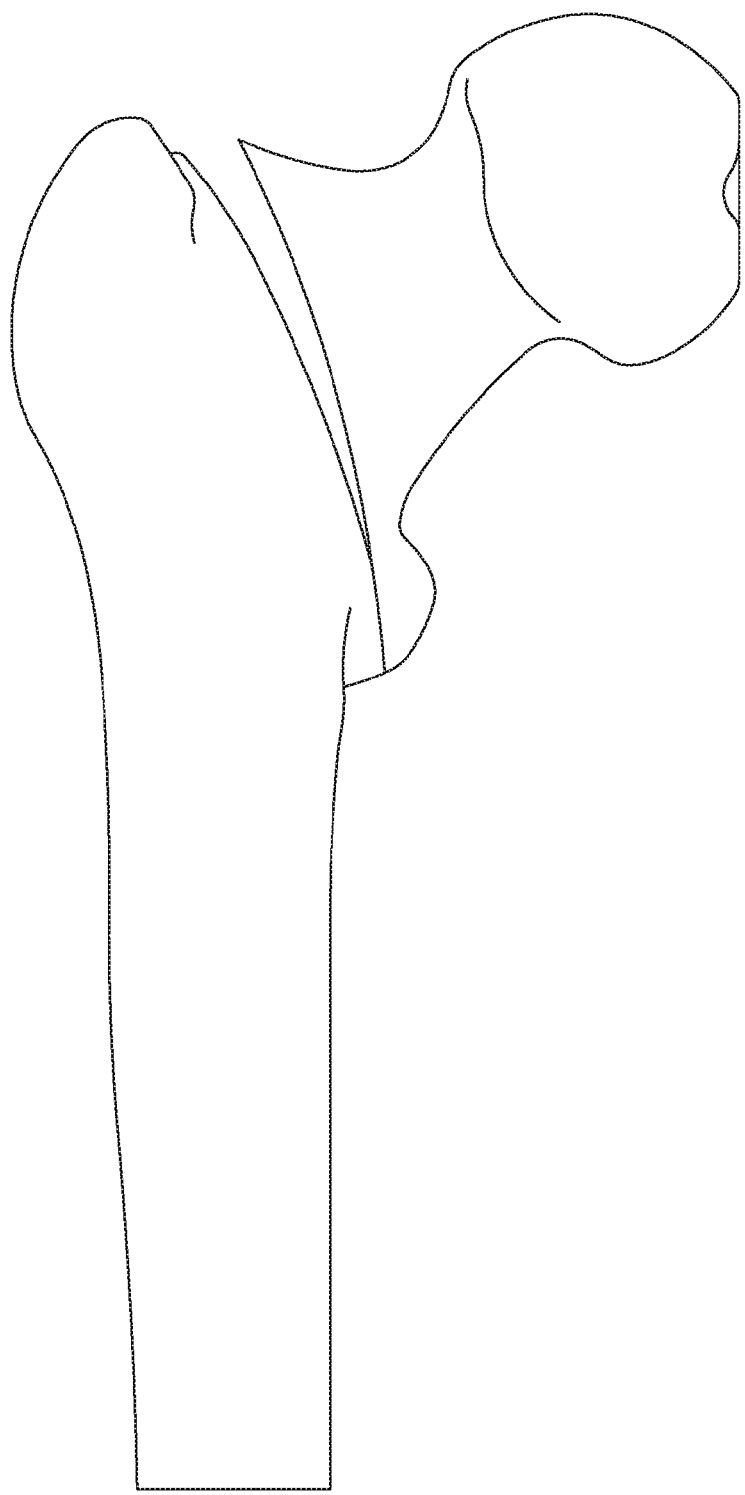
FIGS. 11-14 are schematic views showing the novel interlocking intramedullary rod assembly of FIGS. 9 and 10 being used to reduce a fracture in the femoral neck.

FIGS. 11-14 show interlocking intramedullary rod assembly 205 being deployed in a patient. For the purposes of example but not limitation, the deployment of interlocking intramedullary rod assembly 205 will be discussed in the context of a fracture extending across the femoral neck (FIG. 11). However, it should be appreciated that interlocking intramedullary rod assembly 205 may also be used to treat subtrochanteric fractures, e.g., a fracture extending across the shaft of the proximal femur.

First, the femur is prepared to receive interlocking intramedullary rod assembly 205, i.e., the intramedullary canal is cleared.

Figure 12:
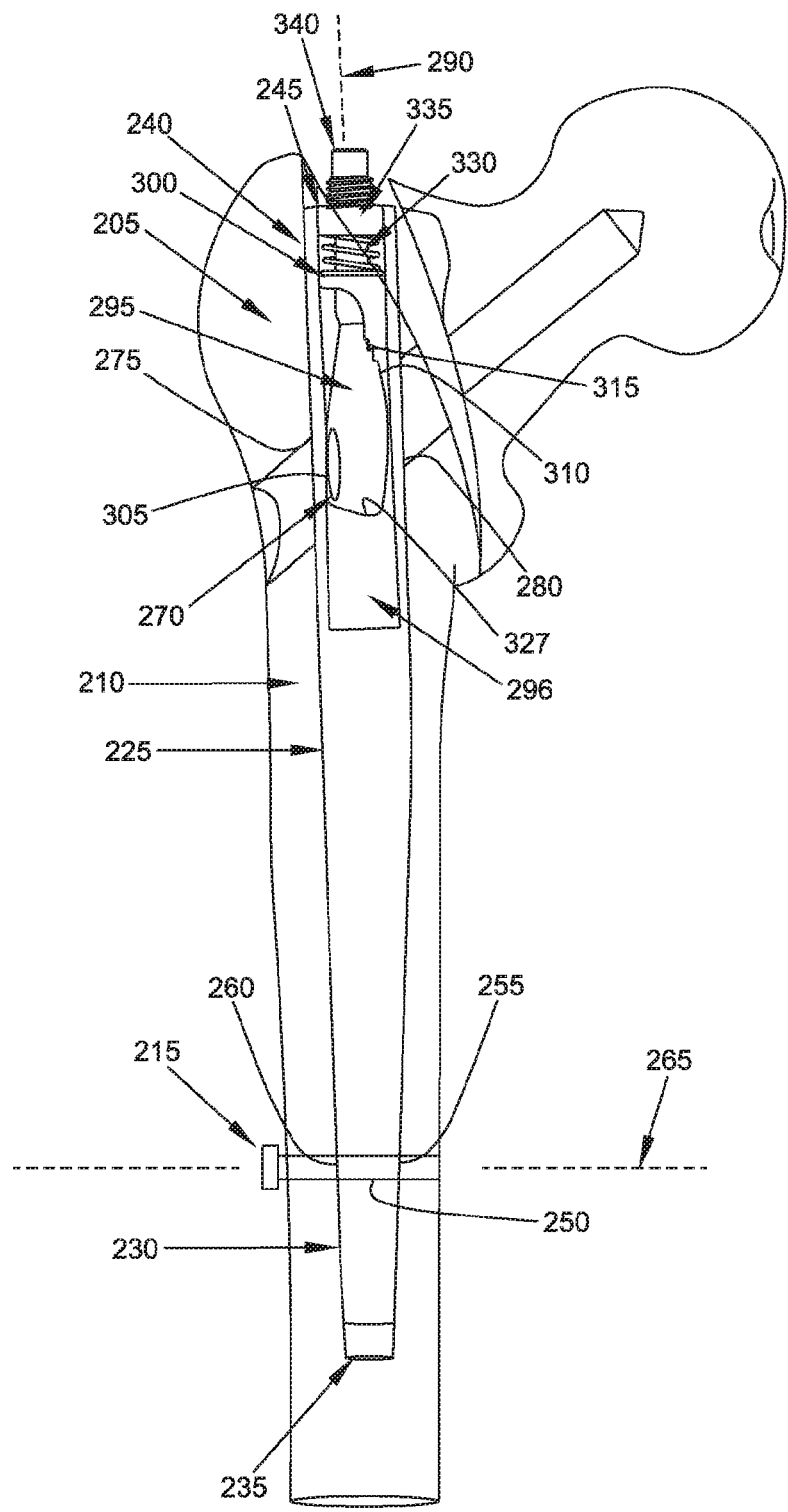

Second, intramedullary rod 210 is inserted into the intramedullary canal of the femur as shown in FIG. 12.

Third, a hole is drilled across the trochanter into the femoral head, passing through dynamic proximal seat 270 in proximal section 240 of intramedullary rod 210. If desired, this hole can be formed by first advancing a guidewire through the bone (and intramedullary rod 210) and then advancing a cannulated drill over the guidewire. Typically this hole is drilled adjacent to the proximal end of lateral slot 275. But note that this hole can also be drilled in the middle of the lateral slot 295, depending on patient anatomy, fracture configuration and the amount of correction needed to reduce the fracture. This opportunity to form the bone hole anywhere along the length of lateral slot 275 effectively creates a "polyaxial" or "variable angle" proximal interlocking screw at insertion. Then proximal interlocking screw 220 is inserted, lateral-to-medial, through a lateral portion of the femur, across dynamic proximal seat 270 in proximal section 240 of intramedullary rod 210 and then into the medial portion of the femur. Note that the bone hole can be formed so that the proximal interlocking screw 220 can be inserted in any part of the lateral slot 275 depending on patient anatomy, fracture configuration and the amount of correction needed to reduce the fracture. This is at the discretion of the surgeon. The proximal interlocking screw 220 passes through the round opening 280 on the medial side of the nail until the threaded distal end of proximal interlocking screw 220 is secured in the femoral head. As this occurs, the advancing proximal interlocking screw 220 passes through cylindrical opening 305 in carrier 295. The proximal interlocking screw 220 is thus a "polyaxial" or "variable angle" screw, in the sense that it may be inserted in any part of the lateral slot 275, and hence may be inserted at a range of angles relative to intramedullary rod 210. Once proximal interlocking screw 220 has been deployed in the bone (and hence across intramedullary rod 210), set screw 325 may be advanced within carrier 295 so as to engage proximal interlocking screw 220 and thereby lock proximal interlocking screw 220 against rotation relative to intramedullary rod 210 (while still allowing proximal interlocking screw 220 to move longitudinally relative to intramedullary rod 210).

Fourth, distal interlocking screw 215 is inserted, lateral-to-medial, through a lateral portion of the femur, across static distal seat 250 in distal section 230 of intramedullary rod 210 and into a medial portion of the femur. Note that distal interlocking screw 215 is securely mounted to distal section 230 of intramedullary rod 210 (by virtue of the disposition of distal interlocking screw 215 in circular openings 255, 260 of intramedullary rod 210) as well as to the lateral and medial portions of the femur.

Figure 13:
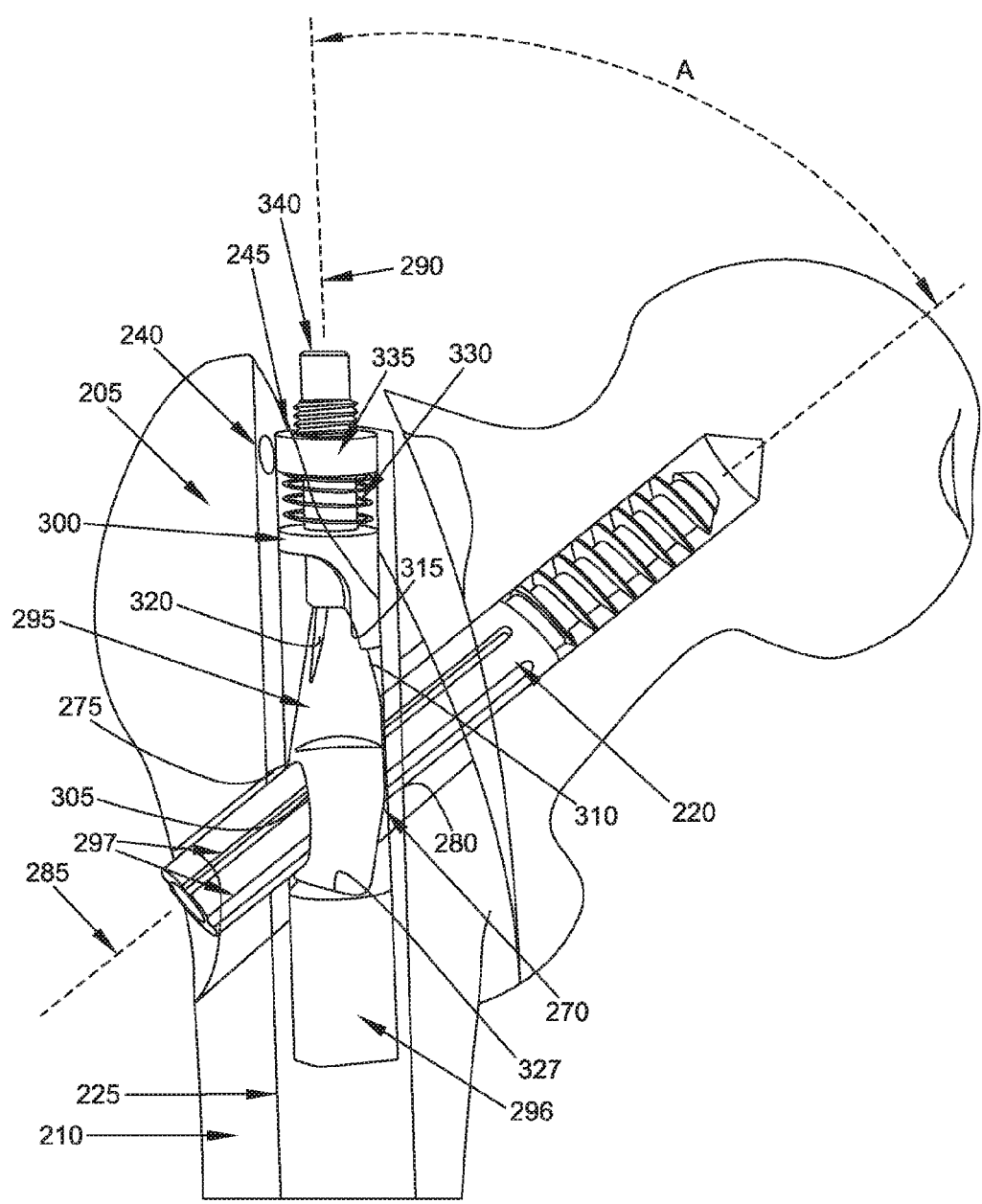

At this point, interlocking intramedullary rod assembly 205 and the femur are in the position shown in FIG. 13.

If desired, the surgeon can use proximal interlocking screw 220 to create linear compression of the fracture site, i.e., by withdrawing proximal interlocking screw 220 relative to intramedullary rod 210 after the screw has been fixed in the femoral head. When backward force is applied on the proximal interlocking screw 220, the entire screw (along with the proximal fractured piece of bone) is pulled back and creates linear compression.

Figure 14:
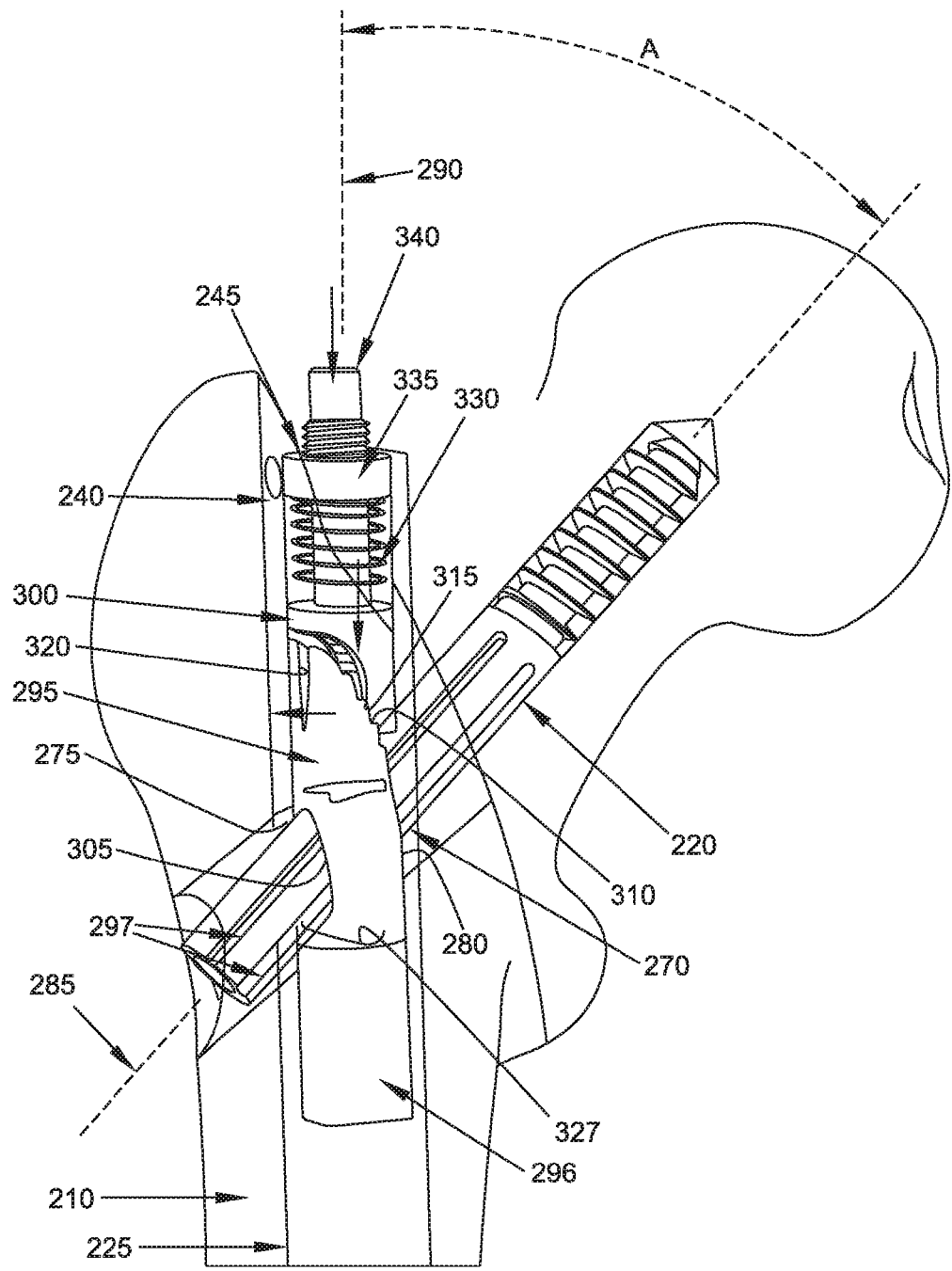

Upon the application of force to the proximal end of the femur (of weight to the proximal end of the femur subsequent to the procedure), the stress at the fracture site increases. Since the medial portion of dynamic proximal seat 270 is circular (i.e., round hole 280), the medial portion of dynamic proximal seat 270 acts as a static hole, preventing any kind of angular motion between proximal interlocking screw 220 and the medial wall of the femur. However, since the lateral portion of dynamic proximal seat 270 is a slot (i.e., slot opening 275), proximal interlocking screw 220 will slide inferiorly in lateral slot opening 275. This will create an angular collapse of the fracture site (FIG. 14). Significantly, as this angular collapse of the fracture site occurs, proximal interlocking screw 220 pivots carrier 295 clockwise (from the angle of view of FIGS. 9, 10, 13 and 14) within intramedullary rod 210. As this occurs, spring 330 moves stepper 300 distally, keeping the ridged distal surface 315 of stepper 300 engaged with the ridged proximal surface 310 of carrier 295. Thereafter, when surgeon-applied force or weight-applied force is no longer applied to the proximal end of the femur, stepper 300 and carrier 295 prevent the bone from returning to its original fracture disposition, i.e., the spring-based stepper 300 prevents carrier 295 from pivoting counterclockwise (from the angle of view of FIGS. 9, 10, 13 and 14) within intramedullary rod 210, which in turn prevents any upward movement of proximal interlocking screw 220 within slot opening 275 on the lateral side of the femur which prevents the fracture from re-opening.

Significantly, with interlocking intramedullary rod assembly 205, the surgeon is also able to easily reduce the fracture during the procedure in which the interlocking intramedullary rod assembly 205 is deployed. More particularly, the surgeon may use push rod 340 to manually pivot proximal interlocking screw 220 and hence close the angle A between proximal interlocking screw 220 and intramedullary rod 210.

Thus it will be seen that interlocking intramedullary rod assembly 205 creates a dynamic one-way angular collapse of the proximal fracture fragment relative to the distal portion of the femur.

It should be appreciated that the novel interlocking intramedullary rod assembly 205 provides the surgeon with two separate ways to create compression of the fracture, i.e., (i) "linear compression" of the fracture site by withdrawing proximal interlocking screw 220 relative to intramedullary rod 210, and (ii) a dynamic one-way angular collapse of the proximal fracture fragment relative to the distal portion of the femur. Significantly, the apparatus is specifically configured so that the dynamic, one-way angular collapse of the fracture site may be effected via a "polyaxial" or "variable angle" screw insertion, whereby to allow the surgeon to take into account patient anatomy, fracture configuration and the amount of correction needed to reduce the fracture.

Modifications of the Preferred Embodiments

Although the present invention has been described herein with reference to particular embodiments, it is to be understood that these embodiments are merely illustrative of the principles and applications of the present invention. It is, therefore, to be understood that numerous modifications may be made to the illustrative embodiments and that other arrangements may be devised without departing from the spirit and scope of the present invention. This device and application of its components can be used for both proximal and distal fractures of the femur, tibia, and humerus.

What is claimed is:

1. An interlocking intramedullary rod assembly for treating a fracture of a bone, said interlocking intramedullary rod assembly comprising:
    an intramedullary rod comprising a distal section and a proximal section;
    a distal interlocking screw comprising a distal end and a proximal end; and
    a proximal interlocking screw comprising a distal end and a proximal end;
    wherein said distal section of said intramedullary rod comprises a static distal seat for receiving said distal interlocking screw, and said proximal section of said intramedullary rod comprises a dynamic proximal seat for receiving said proximal interlocking screw;
    and further wherein said static distal seat is configured to secure said distal interlocking screw to said intramedullary rod such that said distal interlocking screw cannot move relative to said intramedullary rod, and said dynamic proximal seat is configured to secure said proximal interlocking screw to said intramedullary rod such that the angle between said distal end of said proximal interlocking screw and said proximal section of said intramedullary rod can be reduced but not increased;
    the intramedullary rod assembly further comprising a locking mechanism for selectively locking said proximal interlocking screw relative to said intramedullary rod after said proximal interlocking screw has moved relative said intramedullary rod;
    wherein said locking mechanism comprises a carrier pivotally disposed within said intramedullary rod, said carrier comprising a cylindrical opening for receiving said proximal interlocking screw therein; and
    the intramedullary rod assembly further comprising a stepper movably disposed within said intramedullary rod, said stepper being spring-biased against said carrier so as to permit said carrier to pivot so as to reduce the angle between said proximal interlocking screw and said proximal section of said intramedullary rod but prevent said carrier from pivoting back so as to increase the angle between said proximal interlocking screw and said proximal section of said intramedullary rod.

2. An interlocking intramedullary rod assembly according to claim 1 wherein said static distal seat comprises a first round opening and a second round opening.

3. An interlocking intramedullary rod assembly according to claim 2 wherein said first round opening is disposed on a first side of said intramedullary rod and said second round opening is disposed on a second side of said intramedullary rod.

4. An interlocking intramedullary rod assembly according to claim 3 wherein said first round opening is aligned with said second round opening along an axis which extends substantially perpendicular to the longitudinal axis of said distal section of said intramedullary rod.

5. An interlocking intramedullary rod assembly according to claim 2 wherein said distal interlocking screw comprises a shaft sized to make a tight fit within said first round opening and said second round opening.

6. An interlocking intramedullary rod assembly according to claim 1 wherein said dynamic proximal seat comprises a round opening and a slot opening.

7. An interlocking intramedullary rod assembly according to claim 6 wherein said round opening of said dynamic proximal seat is disposed on a first side of said intramedullary rod and said slot opening is disposed on a second side of said intramedullary rod.

8. An interlocking intramedullary rod assembly according to claim 7 wherein said round opening of said dynamic proximal seat and the longitudinal center of said slot opening lie along an axis which extends at a non-perpendicular angle to the longitudinal axis of said proximal section of said intramedullary rod.

9. An interlocking intramedullary rod assembly according to claim 6 wherein said proximal interlocking screw comprises a shaft sized to make a tight fit within said round opening of said dynamic proximal seat and a sliding fit with said slot opening.

10. An interlocking intramedullary rod assembly according to claim 1 wherein said proximal interlocking screw comprises screw threads on said distal end of said proximal interlocking screw.

11. An interlocking intramedullary rod assembly according to claim 1 wherein said carrier comprises a ridged proximal end and said stepper comprises a ridged distal end, said ridged proximal end of said carrier and said ridged distal end of said stepper creating a binding fit therebetween.

12. An interlocking intramedullary rod assembly according to claim 1 further comprising a push rod movably mounted to said intramedullary rod for selectively pivoting said proximal interlocking screw relative to said intramedullary rod.

13. An interlocking intramedullary rod assembly according to claim 1 wherein the disposition of said proximal interlocking screw relative to said intramedullary rod can be changed by manipulating a limb containing the bone.

14. An interlocking intramedullary rod assembly according to claim 1 wherein the disposition of said proximal interlocking screw relative to said intramedullary rod can be changed upon the application of weight to a limb containing the bone.

15. An interlocking intramedullary rod assembly according to claim 1 wherein said dynamic proximal seat is configured to engage said proximal interlocking screw so that said proximal interlocking screw is longitudinally movable relative to said intramedullary rod, whereby to permit linear compression of the fracture by moving said proximal interlocking screw relative to said intramedullary rod.

16. An interlocking intramedullary rod assembly according to claim 15 wherein said dynamic proximal seat is configured to engage said proximal interlocking screw so that said proximal interlocking screw is locked against rotation relative to said intramedullary rod.

17. An interlocking intramedullary rod assembly according to claim 1 wherein said dynamic proximal seat is configured so as to enable said proximal interlocking screw to be received in said intramedullary rod at a variety of angles relative to said intramedullary rod so as to permit variable angle proximal interlocking screw insertion.

18. An interlocking intramedullary rod assembly according to claim 1 wherein said dynamic proximal seat is configured to (i) engage said proximal interlocking screw so that said proximal interlocking screw is longitudinally movable relative to said intramedullary rod, whereby to permit linear compression of the fracture by moving said proximal interlocking screw relative to said intramedullary rod, and (ii) enable said proximal interlocking screw to be received in said intramedullary rod at a variety of angles relative to said intramedullary rod so as to permit variable angle proximal interlocking screw insertion.

19. A method for treating a fracture in the proximal femur, said method comprising:
　providing an interlocking intramedullary rod assembly comprising:
　　an intramedullary rod comprising a distal section and a proximal section;
　　a distal interlocking screw comprising a distal end and a proximal end; and
　　a proximal interlocking screw comprising a distal end and a proximal end;
　　wherein said distal section of said intramedullary rod comprises a static distal seat for receiving said distal interlocking screw, and said proximal section of said intramedullary rod comprises a dynamic proximal seat for receiving said proximal interlocking screw;
　　and further wherein said static distal seat is configured to secure said distal interlocking screw to said intramedullary rod such that said distal interlocking screw cannot move relative to said intramedullary rod, and said dynamic proximal seat is configured to secure said proximal interlocking screw to said intramedullary rod such that the angle between said distal end of said proximal interlocking screw and said proximal section of said intramedullary rod can be reduced but not increased;
　positioning said intramedullary rod in the intramedullary canal of the femur so that said distal section of said intramedullary rod resides within the shaft of the femur and said proximal section of said intramedullary rod resides within a proximal portion of the femur;
　inserting said proximal interlocking screw through the proximal portion of the femur, through said dynamic proximal seat and into the proximal portion of the femur, and inserting said distal interlocking screw through the shaft of the femur, through said static distal seat and into the shaft of the femur; and
　adjusting the disposition of said proximal interlocking screw within said dynamic proximal seat so as to at least partially reduce the fracture;
　wherein the disposition of said proximal interlocking screw relative to said intramedullary rod is adjusted by manipulating the limb containing the femur.

20. A method for treating a fracture in the proximal femur, said method comprising:
　providing an interlocking intramedullary rod assembly comprising:
　　an intramedullary rod comprising a distal section and a proximal section;
　　a distal interlocking screw comprising a distal end and a proximal end; and
　　a proximal interlocking screw comprising a distal end and a proximal end;
　　wherein said distal section of said intramedullary rod comprises a static distal seat for receiving said distal interlocking screw, and said proximal section of said intramedullary rod comprises a dynamic proximal seat for receiving said proximal interlocking screw;
　　and further wherein said static distal seat is configured to secure said distal interlocking screw to said intramedullary rod such that said distal interlocking screw cannot move relative to said intramedullary rod, and said dynamic proximal seat is configured to secure said proximal interlocking screw to said intramedullary rod such that the angle between said distal end of said proximal interlocking screw and said proximal section of said intramedullary rod can be reduced but not increased;

positioning said intramedullary rod in the intramedullary canal of the femur so that said distal section of said intramedullary rod resides within the shaft of the femur and said proximal section of said intramedullary rod resides within a proximal portion of the femur;

inserting said proximal interlocking screw through the proximal portion of the femur, through said dynamic proximal seat and into the proximal portion of the femur, and inserting said distal interlocking screw through the shaft of the femur, through said static distal seat and into the shaft of the femur; and adjusting the disposition of said proximal interlocking screw within said dynamic proximal seat so as to at least partially reduce the fracture;

wherein the disposition of said proximal interlocking screw within said dynamic proximal seat is adjusted by weightbearing.

21. A method for treating a fracture in the proximal femur, said method comprising:

providing an interlocking intramedullary rod assembly comprising:
an intramedullary rod comprising a distal section and a proximal section;
a distal interlocking screw comprising a distal end and a proximal end; and
a proximal interlocking screw comprising a distal end and a proximal end;
wherein said distal section of said intramedullary rod comprises a static distal seat for receiving said distal interlocking screw, and said proximal section of said intramedullary rod comprises a dynamic proximal seat for receiving said proximal interlocking screw;
and further wherein said static distal seat is configured to secure said distal interlocking screw to said intramedullary rod such that said distal interlocking screw cannot move relative to said intramedullary rod, and said dynamic proximal seat is configured to secure said proximal interlocking screw to said intramedullary rod such that the angle between said distal end of said proximal interlocking screw and said proximal section of said intramedullary rod can be reduced but not increased;

positioning said intramedullary rod in the intramedullary canal of the femur so that said distal section of said intramedullary rod resides within the shaft of the femur and said proximal section of said intramedullary rod resides within a proximal portion of the femur;

inserting said proximal interlocking screw through the proximal portion of the femur, through said dynamic proximal seat and into the proximal portion of the femur, and inserting said distal interlocking screw through the shaft of the femur, through said static distal seat and into the shaft of the femur; and adjusting the disposition of said proximal interlocking screw within said dynamic proximal seat so as to at least partially reduce the fracture;

wherein:
said interlocking intramedullary rod assembly further comprises:
a carrier movably disposed within said intramedullary rod, said carrier comprising a cylindrical opening for receiving said proximal interlocking screw therein;
a stepper movably disposed within said intramedullary rod, said stepper being spring-based against said carrier so as to permit said carrier to move distally within said intramedullary rod but prevent said carrier from moving proximally within said intramedullary rod; and
a push rod movably mounted to said intramedullary rod for selectively pivoting said proximal interlocking screw relative to said intramedullary rod;
and further wherein the disposition of said proximal interlocking screw within said dynamic proximal seat is adjusted by moving said push rod.

22. A method according to claim 21 wherein said proximal interlocking screw is moved longitudinally relative to said intramedullary rod so as to provide linear compression of the fracture.

23. A method according to claim 21 wherein said proximal interlocking screw is pivoted relative to said intramedullary rod so as to provide angular collapse of the fracture.

24. A method according to claim 21 wherein said proximal interlocking screw is moved longitudinally relative to said intramedullary rod so as to provide linear compression of the fracture, and said proximal interlocking screw is pivoted relative to said intramedullary rod so as to provide angular collapse of the fracture.

25. A method according to claim 21 wherein the insertion of said proximal interlocking screw through the proximal portion of the femur, through said dynamic proximal seat and into the proximal portion of the femur is effected so that the angle between said proximal interlocking screw and said intramedullary rod takes into account at least one of patient anatomy, fracture configuration and the amount of correction needed to reduce the fracture.

* * * * *